United States Patent
Iyer et al.

(10) Patent No.: US 11,406,835 B2
(45) Date of Patent: Aug. 9, 2022

(54) MEDICAL DEVICES AND/OR LEAD EXTENSIONS HAVING FIXATION STRUCTURES WITH RETAINED PORTIONS PROVIDING MEDICAL LEAD FIXATION

(71) Applicant: MEDTRONIC, INC., Minneapolis, MN (US)

(72) Inventors: Rajesh V. Iyer, Eden Prairie, MN (US); Kunal J. Paralikar, Minneapolis, MN (US); Randy S. Roles, Elk River, MN (US)

(73) Assignee: MEDTRONIC, INC., Minneapolis, MN (US)

( * ) Notice: Subject to any disclaimer, the term of this patent is extended or adjusted under 35 U.S.C. 154(b) by 501 days.

(21) Appl. No.: 16/464,672

(22) PCT Filed: Oct. 19, 2017

(86) PCT No.: PCT/US2017/057348
§ 371 (c)(1),
(2) Date: May 28, 2019

(87) PCT Pub. No.: WO2018/102042
PCT Pub. Date: Jun. 7, 2018

(65) Prior Publication Data
US 2019/0314635 A1    Oct. 17, 2019

Related U.S. Application Data

(60) Provisional application No. 62/486,661, filed on Apr. 18, 2017, provisional application No. 62/428,428, filed on Nov. 30, 2016.

(51) Int. Cl.
*A61N 1/375* (2006.01)
*H01R 13/52* (2006.01)
(Continued)

(52) U.S. Cl.
CPC ....... *A61N 1/3754* (2013.01); *H01R 13/5205* (2013.01); *H01R 13/5224* (2013.01);
(Continued)

(58) Field of Classification Search
CPC combination set(s) only.
See application file for complete search history.

(56) References Cited

U.S. PATENT DOCUMENTS 4,328,813 A    5/1982 Ray
4,672,979 A    6/1987 Pohndofr
(Continued)

FOREIGN PATENT DOCUMENTS

DE    4232627    4/1993
EP    2497527    9/2012

OTHER PUBLICATIONS

PCT/US2017/057348 International Search Report and Written Opinion, dated Jan. 31, 2018.

*Primary Examiner* — Shirley X Jian
(74) *Attorney, Agent, or Firm* — Withers & Keys, LLC

(57) ABSTRACT

Medical devices include fixation structures that include retained portions that provide medical lead fixation within the medical devices. Lead extensions include fixation structures that include retained portions that provide medical lead fixation within the lead extensions. A grip that a clinician may grasp and manipulate is engaged with a nose structure of a header block of the medical device or a connector block of a lead extension and manipulation of the grip causes compression of a deformable structure to ultimately create fixation of the lead or lead extension within the header block or the lead within the extension connector block. The deformable structure may be the retained portion of the fixation structure or alternatively may be separate from the fixation structure.

20 Claims, 30 Drawing Sheets

(51) Int. Cl.
   *H01R 13/622*      (2006.01)
   *H01R 24/58*       (2011.01)
   *H01R 107/00*      (2006.01)

(52) U.S. Cl.
   CPC ........... *H01R 13/622* (2013.01); *H01R 24/58* (2013.01); *H01R 2107/00* (2013.01); *H01R 2201/12* (2013.01)

(56) References Cited

U.S. PATENT DOCUMENTS

| | | | |
|---|---|---|---|
| 6,044,304 A | 3/2000 | Baudino | |
| 6,134,477 A | 10/2000 | Knuteson | |
| 6,210,417 B1 | 4/2001 | Baudino et al. | |
| 6,356,792 B1 | 3/2002 | Errico et al. | |
| 7,580,756 B2 | 8/2009 | Schulte et al. | |
| 7,981,119 B2 | 7/2011 | Lando | |
| 7,988,674 B2 | 8/2011 | Adams | |
| 7,993,352 B2 | 8/2011 | Black et al. | |
| 8,092,260 B2 * | 1/2012 | Sjostedt | A61N 1/3752 439/669 |
| 8,182,540 B2 | 5/2012 | Lin | |
| 8,556,860 B2 | 10/2013 | Stratton | |
| 8,738,151 B2 | 5/2014 | Nelson | |
| 10,238,880 B2 * | 3/2019 | Thom | A61N 1/3605 |
| 2004/0102828 A1 * | 5/2004 | Lowry | A61N 1/0534 607/116 |
| 2005/0222634 A1 * | 10/2005 | Flickinger | A61N 1/3752 607/37 |
| 2007/0250077 A1 | 10/2007 | Skakoon et al. | |
| 2008/0009198 A1 * | 1/2008 | Marino | H01R 35/00 439/668 |
| 2012/0157924 A1 | 6/2012 | Schutz | |
| 2015/0119964 A1 | 4/2015 | Janzig | |
| 2016/0129267 A1 * | 5/2016 | Thom | A61N 1/3752 607/116 |

* cited by examiner

MEDICAL DEVICES AND/OR LEAD EXTENSIONS HAVING FIXATION STRUCTURES WITH RETAINED PORTIONS PROVIDING MEDICAL LEAD FIXATION

RELATED APPLICATIONS

The present application is a U.S. National Stage Application of PCT/US2017/057348, filed on Oct. 19, 2017, which claims priority to U.S. Provisional Application No. 62/486,661 filed on Apr. 18, 2017, and U.S. Provisional Application No. 62/428,428 filed on Nov. 30, 2016.

TECHNICAL FIELD

Embodiments relate to medical devices and/or lead extensions that receive medical leads. More particularly, embodiments relate to medical devices and/or lead extensions that include fixation structures with retained portions to provide fixation of the medical leads that have been inserted into the medical devices or lead extensions.

BACKGROUND

Medical devices that provide a medical function such as electrical stimulation are often affixed to the body at a position of convenience. This is particularly true for implantable medical devices where the device is implanted in a convenient location that may be some distance from a target site within the body where the medical therapy is to be applied. A medical lead is attached to the medical device and is routed to the target site within the body.

The medical lead for electrical stimulation provides electrical contacts on a proximal end and electrodes on a distal end with conductors inside a lead body where those conductors interconnect proximal contacts to distal electrodes that are in contact with the body tissue. The lead is typically attached to the medical device by the proximal end of the lead being inserted into a bore within a header block of the medical device. The proximal contacts of the lead become electrically coupled to electrical connectors within the header block so that stimulation signals pass from the electrical connectors to the proximal contacts and then through the conductors to the distal electrodes.

To fix the lead within the bore, a set screw within a set screw block of the header block is tightened onto a metal ring on the proximal end of the medical lead that is present within the bore of the header block. While the set screw adequately fixes the position of the proximal end of the lead within the bore of the header block, using a set screw for lead fixation presents some drawbacks. For instance, in most cases a clinician must use a tool to tighten the set screw because the set screw cannot be adequately gripped and because the set screw becomes countersunk within the set screw block as the set screw is tightened. Furthermore, the set screw presents a connection that potentially exposes the interior of the header block to fluid ingress.

In some cases, the distance from the medical device to the target site requires a proximal end of a lead extension to be connected to the medical device and then the proximal end of the lead connects to a connector block on a distal end of the lead extension. In such a situation, the same drawbacks discussed above are also present for the connection of the lead extension to the medical device. Additionally, considering the same fixation method such as using set screws may be used to secure the lead to the connector block of the lead extension, the same drawbacks discussed above are also present for that connection.

SUMMARY

Various embodiments address issues such as these and others by providing a medical device that includes a fixation structure to establish lead fixation. The fixation structure includes a grip portion and another portion that is retained by the grip portion but is movable relative to the grip portion. The portion retained by the grip may be a deformable portion or may instead contact a separate deformable structure. When the grip is manipulated, a compression force is applied to the deformable portion of the fixation structure or to a separate deformable structure which then applies a radial force to the proximal end of the lead within a header bore or an extension connector block bore. Thus, the fixation structure provides fixation of the proximal end of the lead, including the proximal end of lead extensions, within the header block. In one or more embodiments, the deformable portion or separate deformable structure may also provide a sealing function to prevent the ingress of fluids around the lead and into the header bore or extension connector block bore.

Various embodiments address issues such as these and others by providing a lead extension that includes a fixation structure to establish lead fixation to the lead extension. The fixation structure of the lead extension may utilize the same structures and techniques as those provided for the medical device.

Embodiments provide a method of fixing a proximal end of medical lead into a bore of a medical device. The method involves inserting the proximal end of the medical lead into the bore. The method also involves applying force to a fixation structure that is movable relative to the bore, the fixation structure including a grip portion that receives the applied force and a deformable portion that is retained by the grip portion and that is within and constrained relative to the bore by the medical device. Applying force to the fixation structure causes compression of the deformable portion so that the deformable portion engages the lead within the bore to fix the position of the lead as the deformable portion compresses.

Embodiments provide a medical device that includes a header block having a bore with an engagement surface and a plurality of electrical connectors within the bore. The medical device also includes a fixation structure mechanically engaged with the engagement surface of the header block, the fixation structure including a grip portion and a deformable portion that is retained by the grip portion. The deformable portion provides a compression force in a radial direction of the bore when a force is applied from the grip portion to the deformable portion.

Embodiments provide a medical system that includes a medical device having a stimulation circuit and a header block, the header block having a bore with an engagement surface and a plurality of electrical connectors within the bore that are electrically coupled to the stimulation circuit. The medical device further includes a fixation structure mechanically engaged with the engagement surface of the header block, the fixation structure including a grip portion and a deformable portion that is retained by the grip portion and is constrained by the header block, the deformable portion providing a compression force in a radial direction of the bore when a force is applied from the grip portion to the deformable portion. The medical system further includes a medical lead having a lead body surrounding electrical conductors, the lead body having a proximal region positioned within the bore of the header block, the proximal region having a plurality of contacts that engage corresponding electrical connectors in the bore and engage the conductors within the lead body. The deformable portion of the fixation structure is compressed into contact with a portion of the proximal region of the medical lead to fix the medical lead within the bore.

Embodiments provide a method of fixing a proximal end of medical lead into a bore of a medical device. The method involves inserting the proximal end of the medical lead into the bore. The method further involves applying force to a fixation structure that is movable relative to the bore and is in contact with a deformable structure that is present within the bore and constrained by the medical device, the fixation structure including a grip portion that receives the applied force and a ferrule portion that is retained by the grip portion and that is within the bore and that contacts the deformable structure. Applying force to the fixation structure causes compression of the deformable structure so that the deformable structure engages the lead within the bore to fix the position of the lead as the deformable structure compresses.

Embodiments provide a medical device that includes a header block having a bore with an engagement surface and a plurality of electrical connectors within the bore. The medical device further includes a fixation structure mechanically engaged with the engagement surface of the header block, the fixation structure including a grip portion and a ferrule portion that is retained by the grip portion and is in contact with a deformable structure that is within the bore. The deformable structure provides a compression force in a radial direction of the bore when a force is applied from the grip portion to the ferrule portion.

Embodiments provide a medical system that includes a medical device having a stimulation circuit and a header block, the header block having a bore with an engagement surface and a plurality of electrical connectors within the bore that are electrically coupled to the stimulation circuit. The medical device further includes a fixation structure mechanically engaged with the engagement surface of the header block, the fixation structure including a grip portion and a ferrule portion that is retained by the grip portion and is in contact with a deformable structure that is within the bore, the deformable structure providing a compression force in a radial direction of the bore when a force is applied from the grip portion to the ferrule portion. The medical system further includes a medical lead having a lead body surrounding electrical conductors, the lead body having a proximal region positioned within the bore of the header block, the proximal region having a plurality of contacts that engage corresponding electrical connectors in the bore and engage the conductors within the lead body. The deformable structure is compressed into contact with a portion of the proximal region of the medical lead to fix the medical lead within the bore.

Embodiments provides a method of fixing a proximal end of medical lead into a bore of a lead extension. The method involves inserting the proximal end of the medical lead into the bore and applying force to a fixation structure that is movable relative to the bore. The fixation structure includes a grip portion that receives the applied force and a deformable portion that is retained by the grip portion and that is within and constrained relative to the bore by the lead extension. Applying force to the fixation structure causes compression of the deformable portion so that the deformable portion engages the lead within the bore to fix the position of the lead as the deformable portion compresses.

Embodiments provide a lead extension that includes a connector block having a bore with an engagement surface and a plurality of electrical connectors within the bore. The lead extension includes a fixation structure mechanically engaged with the engagement surface of the connector block, the fixation structure including a grip portion and a deformable portion that is retained by the grip portion, the deformable portion providing a compression force in a radial direction of the bore when a force is applied from the grip portion to the deformable portion.

Embodiments provide a medical system that includes a medical device having a stimulation circuit and a header block, the header block having a bore with an engagement surface and a plurality of electrical connectors within the bore that are electrically coupled to the stimulation circuit. The medical system includes a lead extension having a connector block on a distal region and having and a body surrounding electrical conductors, the connector block having a bore with an engagement surface and a plurality of electrical connectors within the bore, the body having a proximal region positioned within the bore of the header block, the proximal region having a plurality of contacts that engage corresponding electrical connectors in the bore of the header block and engage the conductors within the body, the conductors within the body engaging connectors of the connector block. The lead extension further includes a fixation structure mechanically engaged with the engagement surface of the connector block, the fixation structure including a grip portion and a deformable portion that is retained by the grip portion and is constrained by the connector block, the deformable portion providing a compression force in a radial direction of the bore when a force is applied from the grip portion to the deformable portion. The medical system further includes a medical lead having a lead body surrounding electrical conductors, the lead body having a proximal region positioned within the bore of the connector block, the proximal region of the lead body having a plurality of contacts that engage corresponding electrical connectors in the bore of the connector block and engage the conductors within the lead body, the deformable portion of the fixation structure being compressed into contact with a portion of the proximal region of the lead body to fix the medical lead within the bore of the connector block.

Embodiments provide a method of fixing a proximal end of medical lead into a bore of a lead extension. The method involves inserting the proximal end of the medical lead into the bore and applying force to a fixation structure that is movable relative to the bore and is in contact with a deformable structure that is present within the bore and constrained by the lead extension. The fixation structure includes a grip portion that receives the applied force and a ferrule portion that is retained by the grip portion and that is within the bore and that contacts the deformable structure, wherein applying force to the fixation structure causes compression of the deformable structure so that the deformable structure engages the lead within the bore to fix the position of the lead as the deformable structure compresses.

Embodiments provide a lead extension that includes a connector block having a bore with an engagement surface and a plurality of electrical connectors within the bore. The lead extension includes a fixation structure mechanically engaged with the engagement surface of the connector block, the fixation structure including a grip portion and a ferrule portion that is retained by the grip portion and is in contact with a deformable structure that is within the bore, the deformable structure providing a compression force in a radial direction of the bore when a force is applied from the grip portion to the ferrule portion.

Embodiments provide a medical system that includes a medical device having a stimulation circuit and a header block, the header block having a bore with an engagement surface and a plurality of electrical connectors within the bore that are electrically coupled to the stimulation circuit. The medical system includes a lead extension having a connector block on a distal region and having and a body surrounding electrical conductors, the connector block having a bore with an engagement surface and a plurality of electrical connectors within the bore, the body having a proximal region positioned within the bore of the header block, the proximal region having a plurality of contacts that engage corresponding electrical connectors in the bore of the header block and engage the conductors within the body, the conductors within the body engaging connectors of the connector block. The lead extension includes a fixation structure mechanically engaged with the engagement surface of the connector block, the fixation structure including a grip portion and a ferrule portion that is retained by the grip portion and is in contact with a deformable structure that is within the bore of the lead extension, the deformable structure providing a compression force in a radial direction of the bore when a force is applied from the grip portion to the ferrule portion. The medical system includes a medical lead having a lead body surrounding electrical conductors, the lead body having a proximal region positioned within the bore of the connector block, the proximal region having a plurality of contacts that engage corresponding electrical connectors in the bore of the connector block and engage the conductors within the lead body, the deformable structure being compressed into contact with a portion of the proximal region of the medical lead to fix the medical lead within the bore of the connector block.

DETAILED DESCRIPTION

Embodiments provide medical devices and/or lead extensions with a fixation structure mechanically engaged with a header block of a medical device and/or with a connector block of a lead extension, respectively. A deformable portion of the fixation structure or a separate deformable structure is within a bore of the header block and/or within a bore of the connector block. Manipulation of a grip portion of the fixation structure results in compression of a retained deformable portion of the fixation structure or compression of the separate deformable structure which causes the retained deformable portion or separate deformable structure to apply force radially relative to the bore to contact a proximal region of the lead, including proximal region of a lead extension, that is present within the bore of the header block or within the bore of the connector block of the lead extension. The force being applied by the retained deformable portion or the separate deformable structure to the proximal region of the lead results in fixation of the lead or lead extension within the bore of the header block and/or the fixation of the lead within the bore of the connector block of the lead extension.

Figure 1:
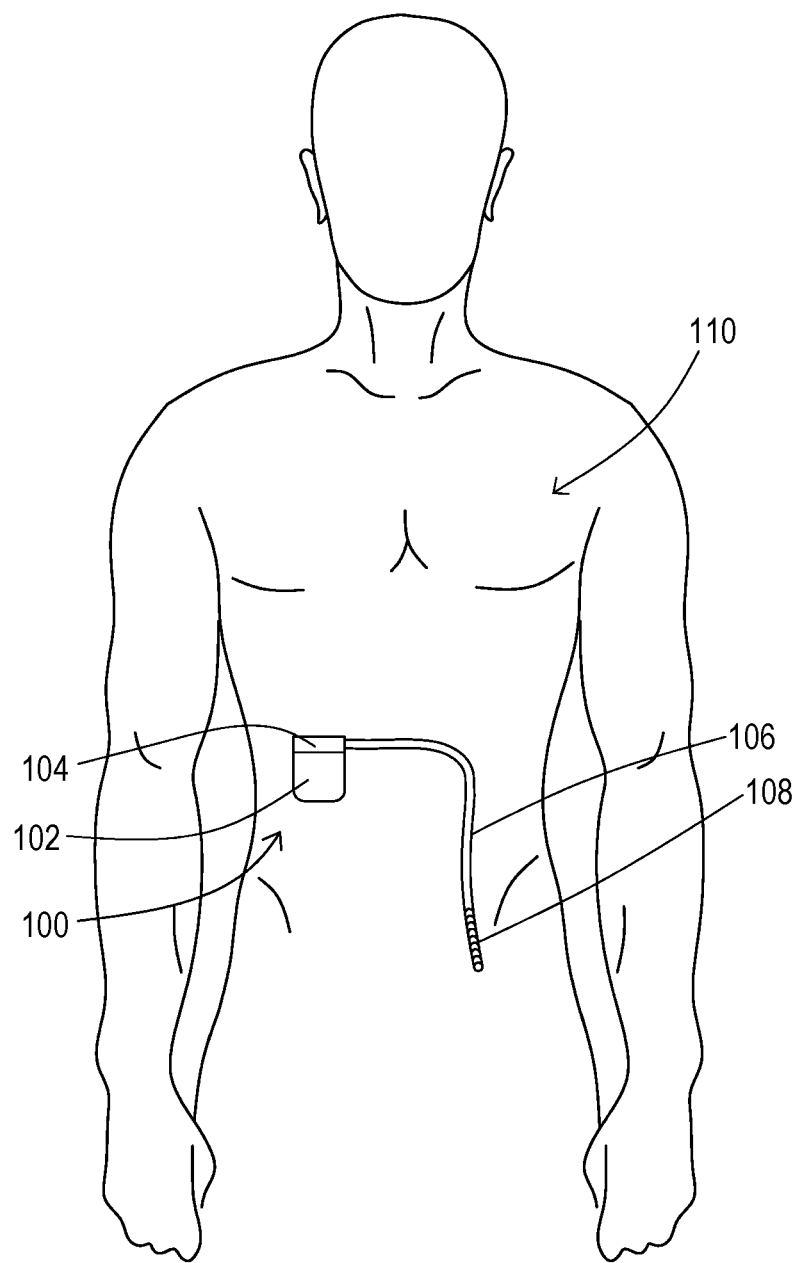
FIG. 1 shows an operating environment for various embodiments where a medical system including a medical device and a medical lead are attached to or implanted into a patient.

FIG. 1 shows a medical system 100 that includes a medical device 102 and a medical lead 106. In this particular example, the medical system 100 including the medical device 102 and the medical lead 106 are implantable. The medical lead 106 includes a proximal end that has been inserted into a bore of a header block 104 of the medical device 102. The distal end of the medical lead 106 includes electrodes 108 that are positioned at a target site where electrical stimulation therapy is to be provided. A lead extension not shown in FIG. 1 may also be present where the proximal end of the lead extension is inserted into the medical device 102, with the lead then being inserted into a connector block on a distal end of the lead extension. In the embodiments below, reference is made to the lead but it will be understood that this also applies to a lead extension being inserted into a header of the medical device. It will also be understood that the specific implant and lead location of FIG. 1 is to show an example and that the embodiments of the fixation structure apply to any implant and lead location.

Additionally, the discussion below for FIGS. 1-10 is with respect to a lead being inserted into a header of the medical device. However, the same fixation structures may also be used for lead extension connector blocks located on the distal end of the lead extension, when one is present, which is discussed in more detail below with reference to FIGS. 11-18. In such a case, the lead is inserted into the lead extension connector block and the fixation structure then maintains the lead within the lead extension connector block. Thus, for a given lead and lead extension combination, two fixation structures may be present where a first fixation structure fixes the proximal end of the lead extension in the header of the medical device while a second fixation structure fixes the proximal end of the lead in the connector block of the lead extension.

Figure 2A:
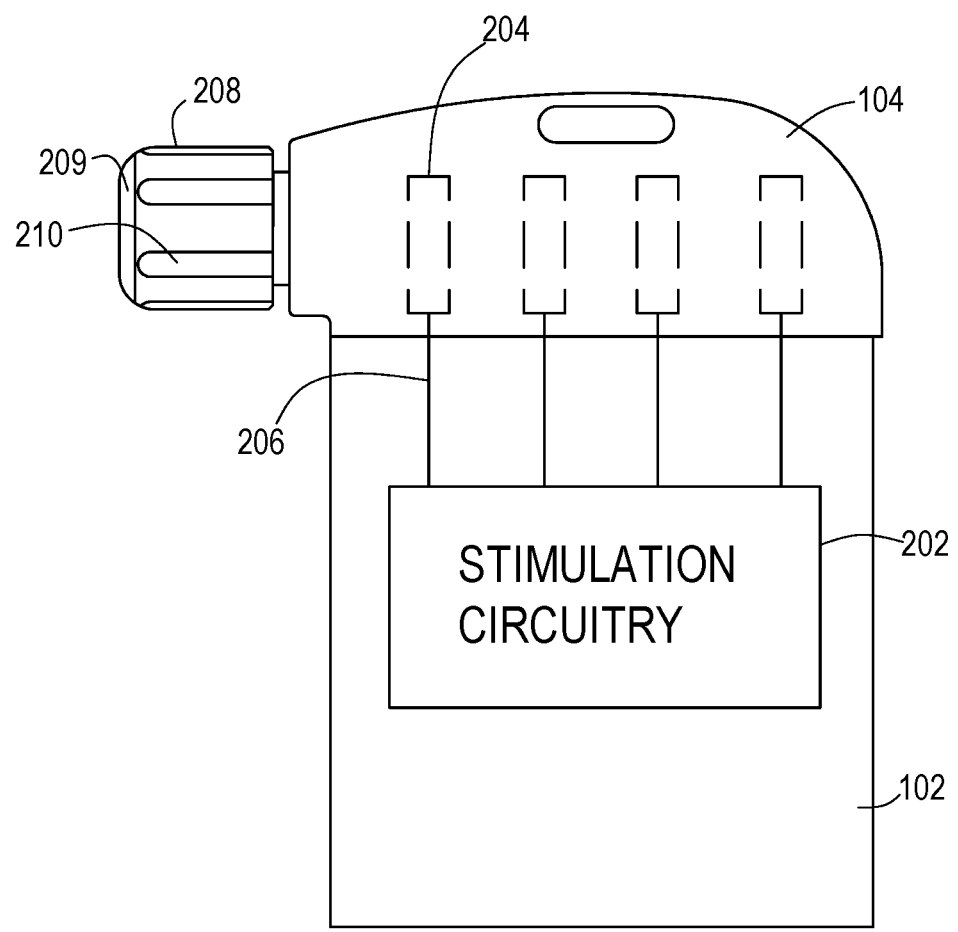
FIG. 2A shows an example of a medical device having a fixation structure with a grip portion that can be manipulated to provide lead fixation.

FIG. 2A shows an example of the medical device 102 and a header block 104 of the medical device 102. The header block 104, as well as the header blocks of the other figures that are discussed herein, may be a separate assembly that is mounted to the medical device 102 or may be integral to the medical device 102 via a common housing. The medical device 102 of this example includes stimulation circuitry 202 that provides electrical stimulation signals via a set of feed through conductors 206 that interconnect with corresponding electrical connectors 204 inside of the header block 104. The medical device 102 of this example also includes a grip portion 208 of a fixation structure that can be grasped and manipulated by a clinician, and thus by hand and without tools, when connecting a lead 106 to the header block 104 of the medical device 102. A cap 209 of the grip portion which is discussed in more detail below is also shown.

Figure 2B:
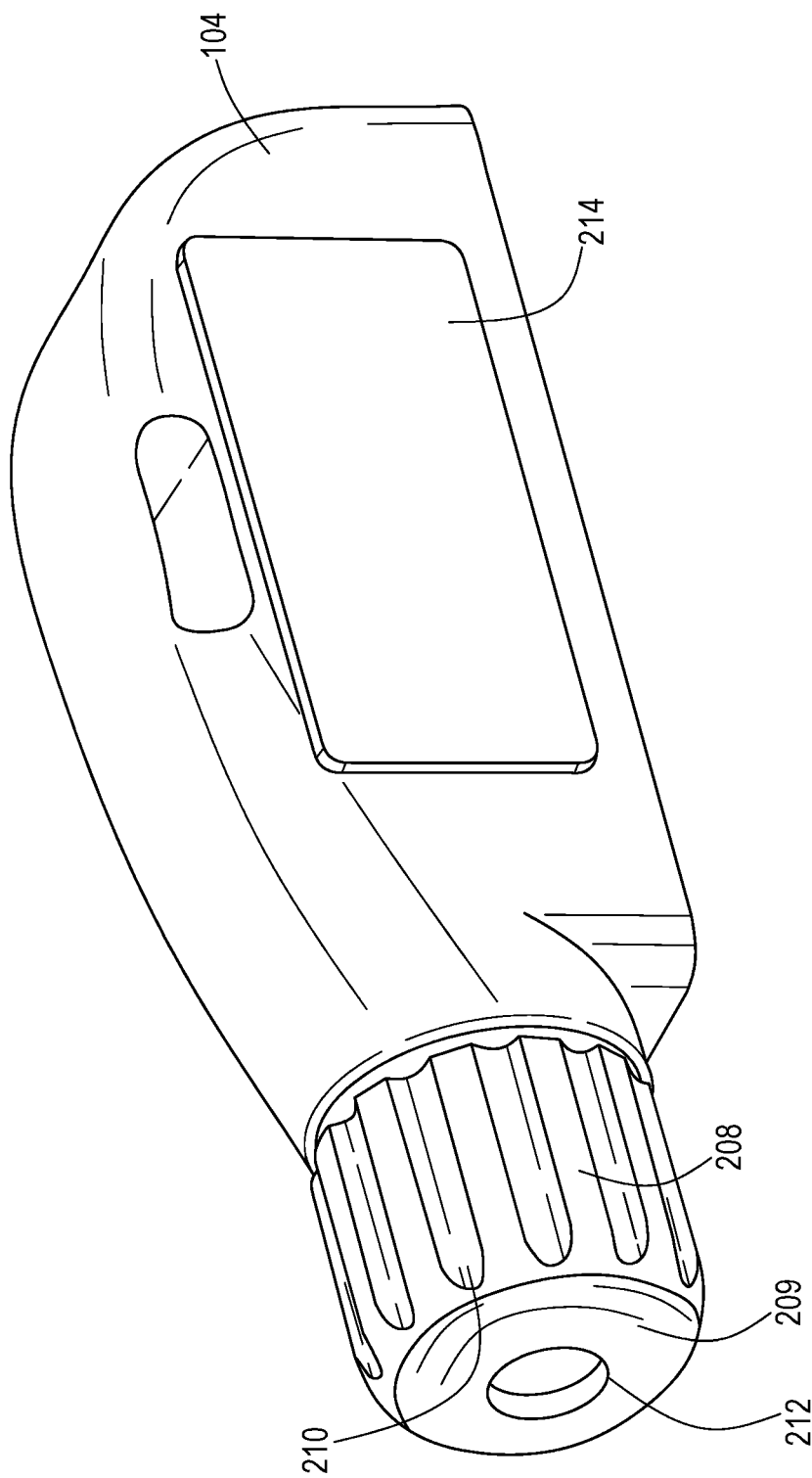
FIG. 2B shows a perspective view of a header block and fixation structure.

The header block 104 and grip portion 208 are also shown in the perspective view of FIG. 2B. As can be seen in FIGS. 2A and 2B, the grip portion 208 may include grooves 210 or other knurled like surface treatments to provide additional friction that aids in grasping and manipulating the grip portion 208. The grip portion 208 is movable relative to the header block 104 which allows the grip portion 208 to be manipulated to provide fixation of the lead 106 that has been inserted into a bore 212 of the grip portion 208 and cap 209 of this example that leads to the bore of the header block 104. In this example, the header block 104 includes a cover 214 that may be installed on to the header block 104 after the internal features of the header block 204 such as electrical connectors and seals are positioned and surrounded with a filler material.

Figure 3A:
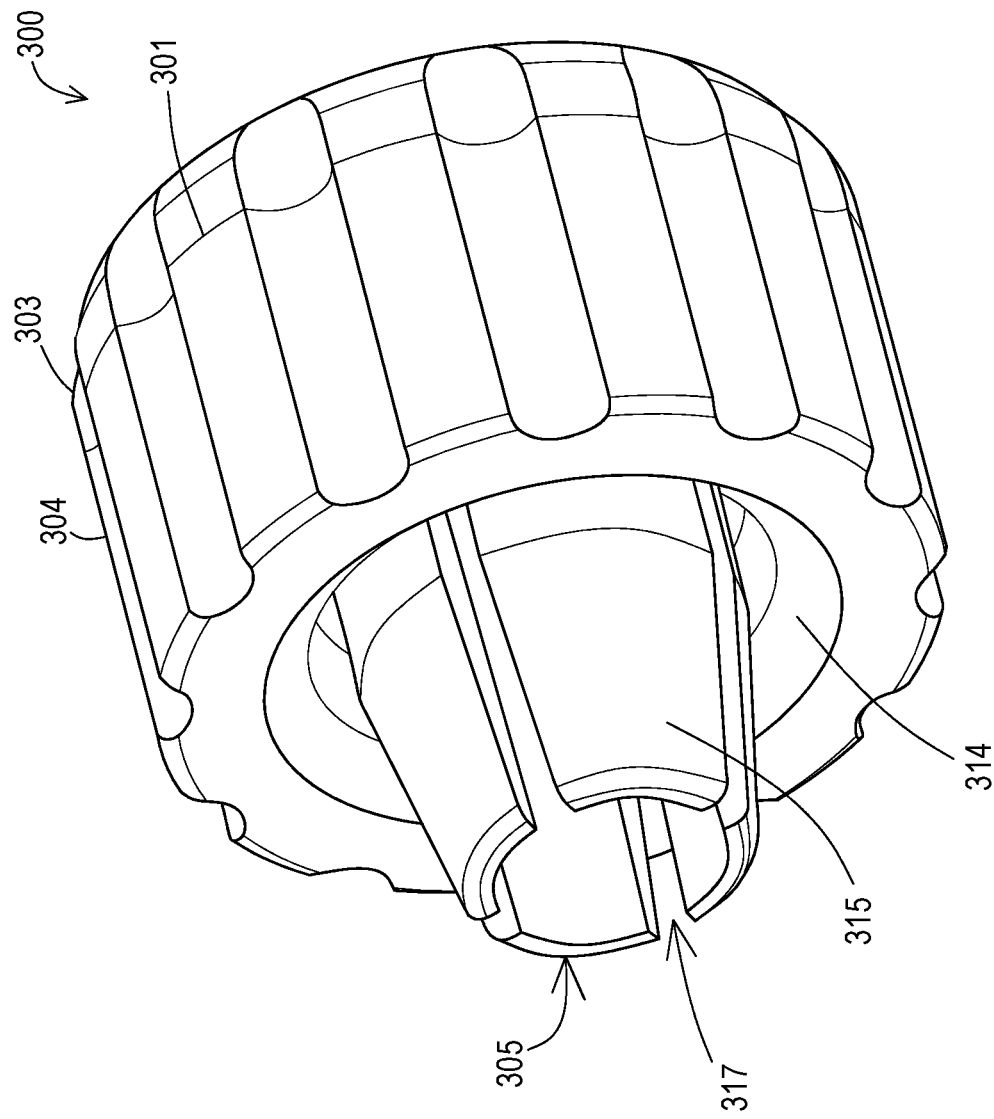
FIG. 3A shows a perspective view of an example of the fixation structure including a grip portion and a deformable portion.

FIG. 3A shows a perspective view of a fixation assembly 300 like that of FIGS. 2A and 2B. The fixation assembly 300 includes a grip portion 304 with a cap 303 attached to the grip portion 304 at a weld seam 301. The reason the cap 303 is present will be apparent from the discussion of FIGS. 3B and 3C below. The grip portion 304 of this example includes threads 314 that engage threads on the header block of the implantable medical device. The fixation structure 300 of this example also includes a deformable portion 305, which in this example provides a conical portion 315 that has slots 317 so that the conical portion 315 acts as a mechanical chuck again the lead. The relationship of the conical portion 315 to the header block of the implantable device is described in further detail below with reference to FIGS. 6A, 6B, 8, and 10.

Figure 3B:
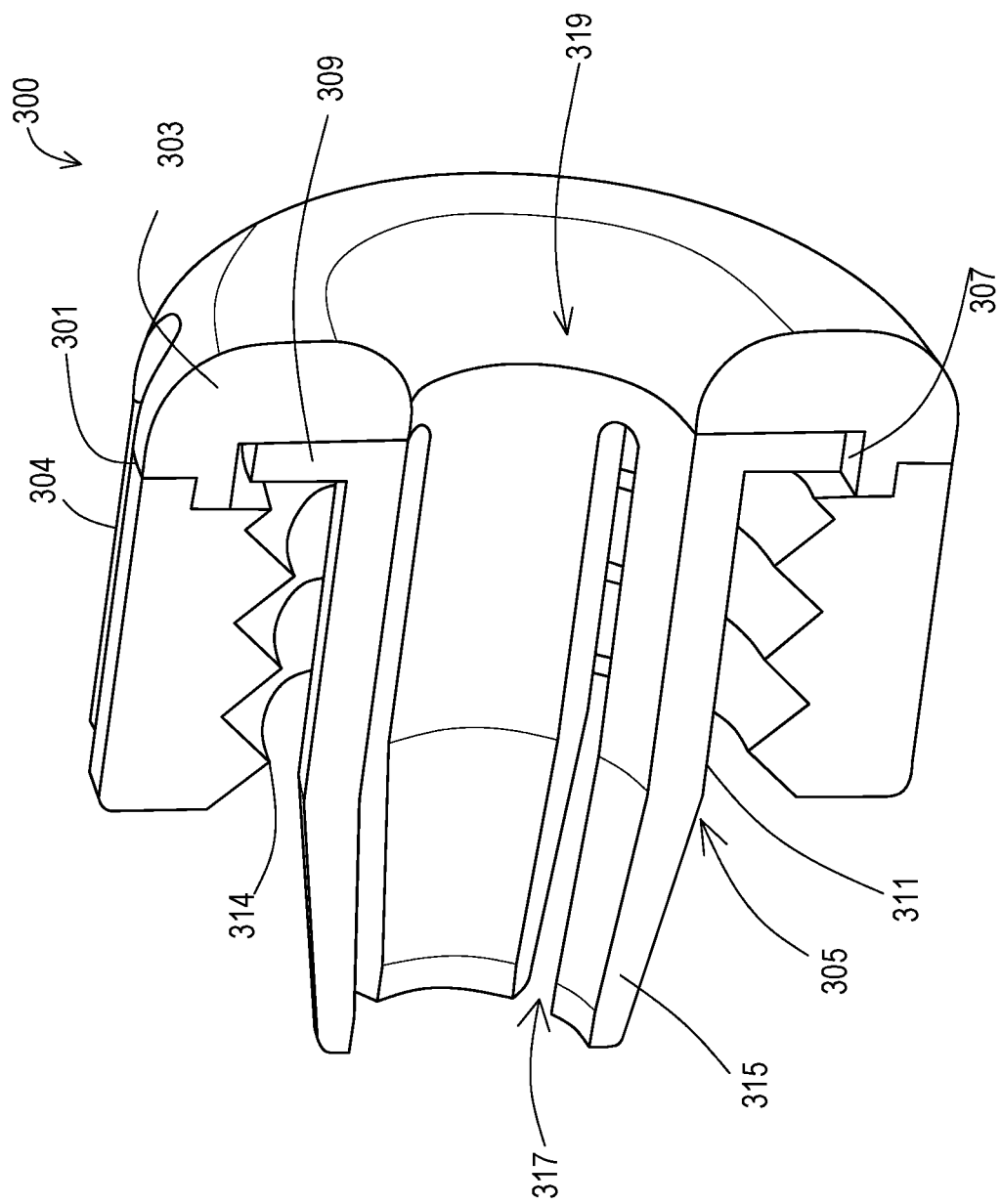
FIG. 3B shows a cross-sectional perspective view of the example of the fixation structure of FIG. 3A.
Figure 3C:
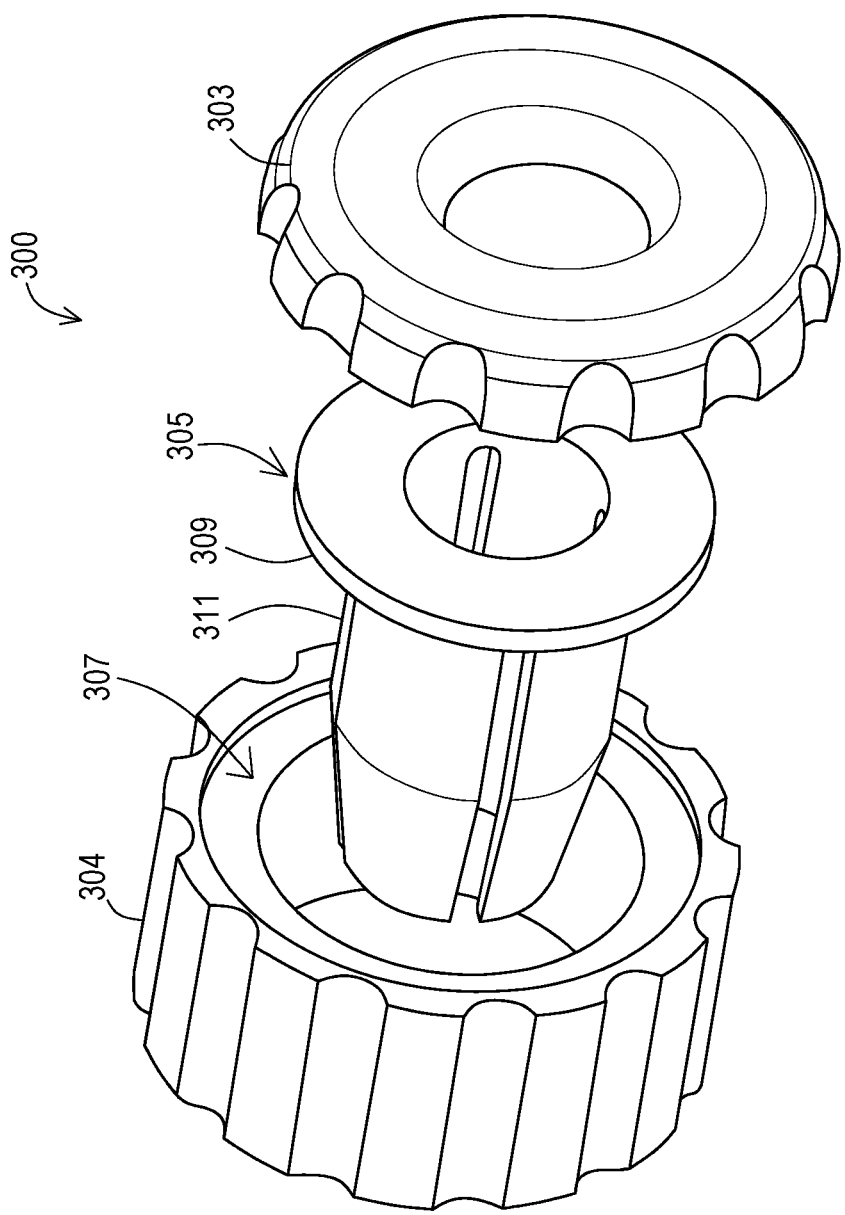
FIG. 3C shows an exploded perspective view of the example of the fixation structure of FIG. 3A.

FIG. 3B shows a cross-sectional view of the fixation structure 300 while FIG. 3C shows an exploded view to demonstrate the manner of assembling the fixation structure 300. Here it can be seen that the deformable portion 305 is retained together with the grip portion 304 due to the presence of a recess 307 in the grip portion 304 where a flange 309 of the deformable portion 305 resides. It can be further seen that the cap 303 that is attached to the grip portion 304 by manner of the weld seam 301 prevents the deformable portion 305 from separating from the grip portion 304. By retaining the deformable portion 305 together with the grip portion 304, a surgeon installing the implantable medical device and lead does not need to deal with the deformable portion 305 and the grip portion 304 separately and there is no concern about the deformable portion 305 inadvertently falling from the bore of the medical device upon the grip portion 304 being removed since the deformable portion 305 remains with the grip portion 304 at all times.

While the deformable portion 304 is retained by the grip portion 305, the flange 309 may fit within the recess 307 with enough clearance to allow the grip portion 305 to rotate about the axis of the bore 319 while the deformable portion 304 remains still. As described below, this allows the deformable portion 304 to engage the interior surfaces of the header block while not restricting the ability of the grip portion 304 to be manually turned by a user when tightening or loosening the grip portion from the header block.

In the example shown, the deformable structure 305 has four slots 317 and includes a ferrule shaped portion 311 that extends between the conical portion 315 and the flange 309. In this example, the ferrule shaped portion 311 transitions into the conical portion 315 at about the same point that the grip portion 304 terminates. It will be appreciated that the ferrule portion 311 may be longer or shorter as may be dictated by the design of the interior surfaces of the header block. It will also be appreciated that any number of slots 317 may be included and the slots 317 may have lengths other than the full lengths shown. For instance, the slots may be primarily in the conical portion 315 rather than running the full length of the ferrule portion 311.

Constructing the fixation structure 300 of course involves placing the deformable structure 305 into the grip portion 305 prior to the cap 303 being welded to the grip portion 305 and with the flange 309 coming to rest within the recess 307. Once the deformable structure 305 is positioned with the flange 309 seated in the recess 307, the cap 303 is then positioned onto the grip portion 304 and the weld seam 301 is created.

Figure 3D:
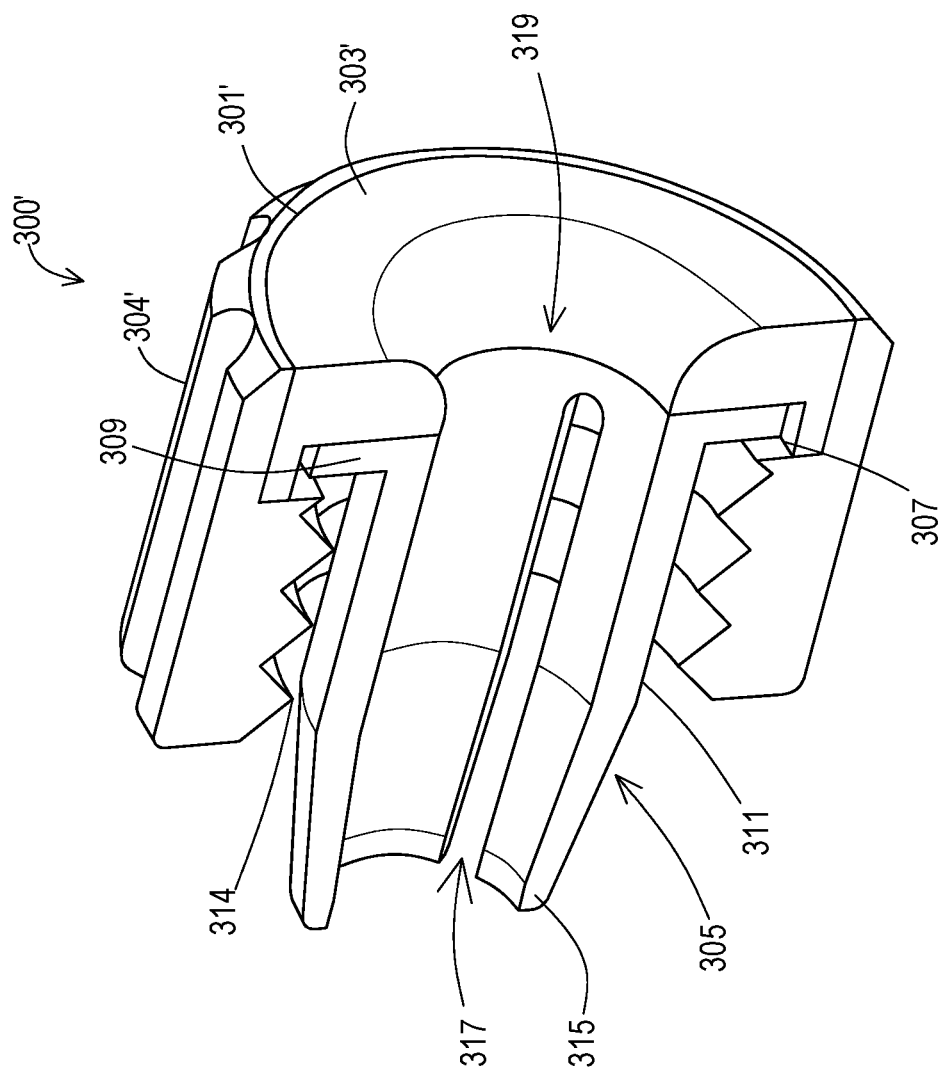
FIG. 3D shows a cross-sectional perspective view of another example of the fixation structure where the grip portion and an associate cap fit together differently.

FIG. 3D shows an alternative fixation structure 300' where the deformable portion 305 is the same as in FIGS. 3A-3C but the grip portion 304' and cap 303' are designed differently. Rather than the cap 303' forming the outer shoulder as in FIGS. 3A-3C, the grip portion 304' forms the outer shoulder and the cap 303' joins the grip portion 304' at a radial position on the blunt end and are bonded together via the weld seam 301'. The grip portion 304' continues to provide the recess 307 where the flange 309 of the deformable portion 305 rests while being retained in place once the cap 303' is joined to the grip portion 304'.

Figure 4A:
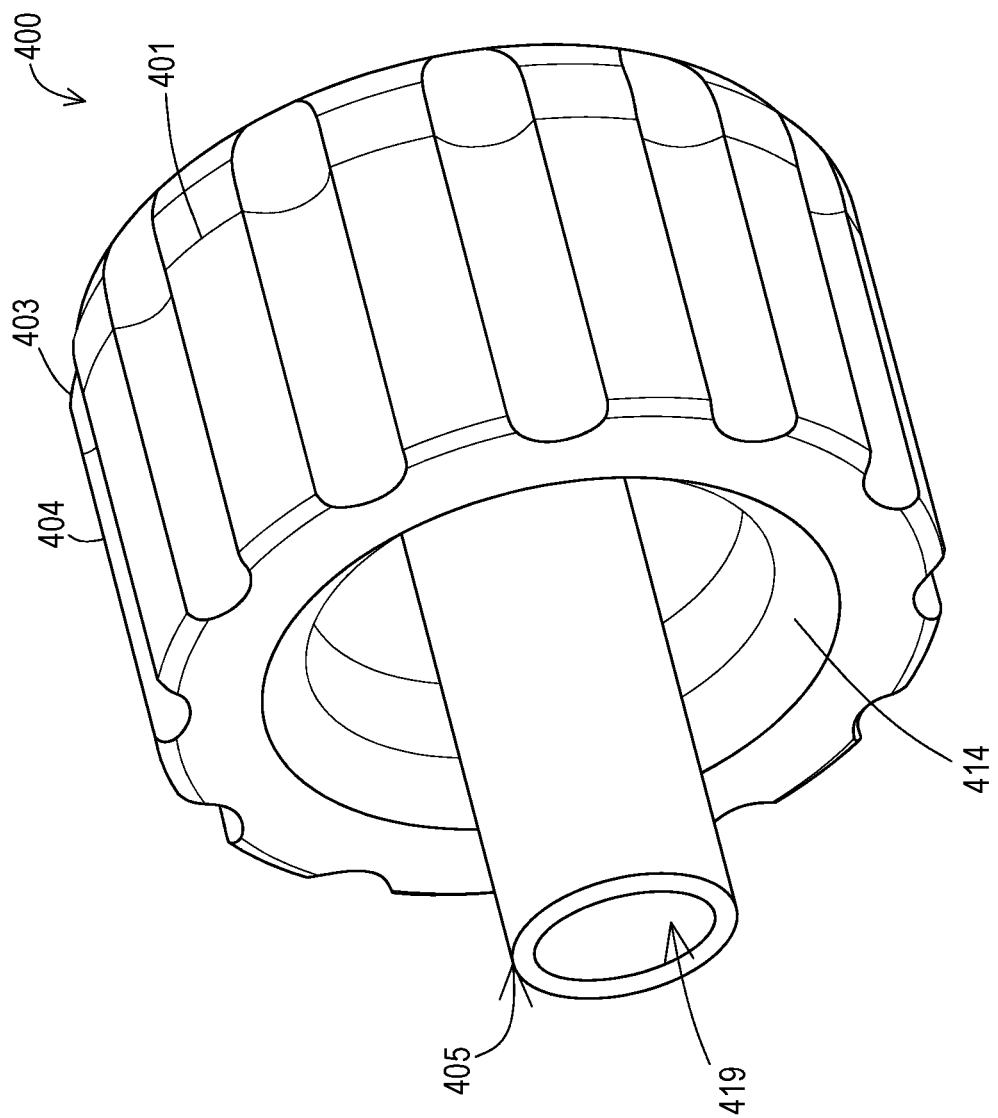
FIG. 4A shows a perspective view of an example of the fixation structure including a grip portion and a ferrule portion.

FIG. 4A shows another embodiment of a fixation structure 400 that includes a grip portion 404 and a ferrule portion 405. This embodiment relies upon a separate deformable structure, not shown in FIG. 4A but shown and described below, to be permanently or temporarily installed within the bore of the implantable medical device. The blunt end of the ferrule portion 405 abuts the deformable structure to cause the separate deformable structure to engage the lead. As shown, the grip portion 404 defines a recess 407 that receives a flange 409 of the ferrule portion 405 so that upon the cap 403 being joined to the grip portion 404 via the weld seam 401, the ferrule portion 405 is retained by the grip portion 404. As with the prior embodiment, the grip portion 404 attached to the header block such as by threads 414 engaging threads of the header block.

Figure 4B:
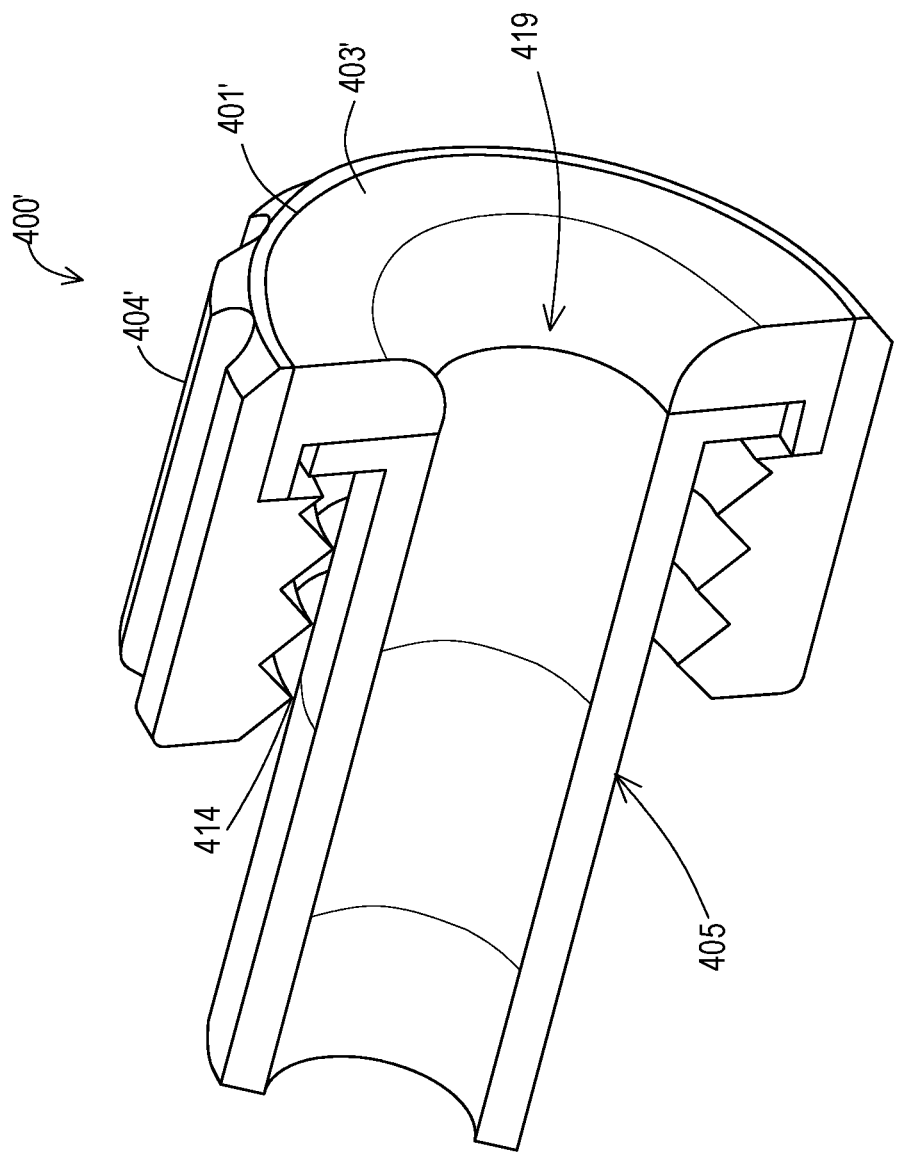
FIG. 4B shows a cross-sectional perspective view of another example of the fixation structure including a grip portion and a ferrule portion.

FIG. 4B shows a cross-section of another embodiment of a fixation structure 400' that includes a grip portion 404' and a ferrule portion 405 like that of FIG. 4A. This fixation structure 400' includes an alternative location of the weld seam 401' between a cap 403' and the grip portion 404' like the weld seam 301' of the embodiment shown above in FIG. 3D.

The grip portions 304, 404 as well as the caps 303, 403 may be constructed of materials including metals such as such as titanium, niobium, titanium-niobium alloys, MP35N® alloy (Ni—Co—Cr—Mo alloy), stainless steel and the like as well as other materials including rigid polymers that are biocompatible. The deformable portion 305 and the ferrule portion 405 may also be constructed of these same materials. While the conical portion 315 of the deformable portion 305 deforms to some degree to compress into the lead body or ring on the lead body, the conical portion 315 may be constructed of metal because slots 317 in the conical portion allow the conical portion to deform to the smaller diameter. Where the deformable portion 305 contacts a metal ring on the lead to provide fixation where that metal ring is an active electrical contact of the stimulation system, then a conductive pathway through the deformable portion 305 to the body of the patient should be avoided by making items in the conduction path such as the deformable portion 305 and/or the grip portions 304, 404; caps 303, 404; and ferrule 405 from a non-conductive material such as a rigid biocompatible polymer. Likewise, the portion of the header block or connector block that houses such an active metal ring should also be constructed of a non-conductive material for the same reason.

Figure 5A:
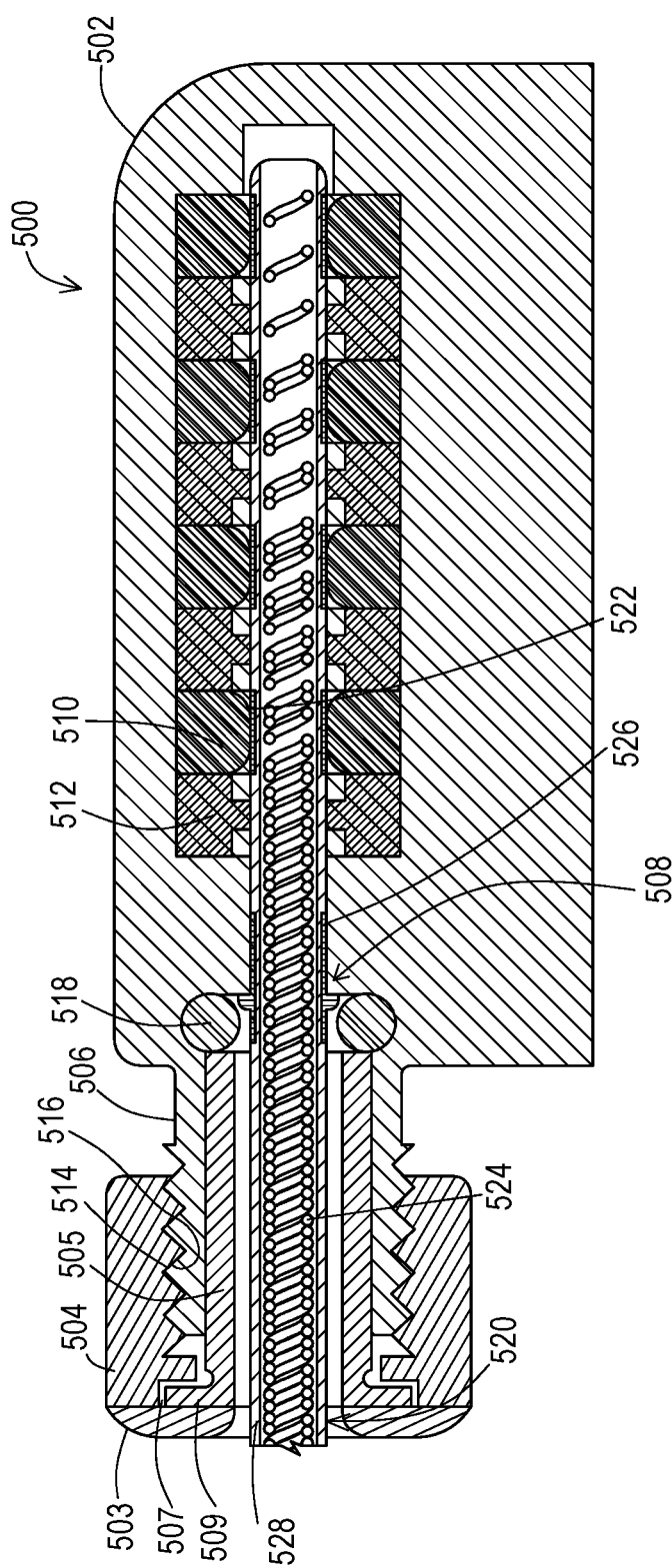
FIG. 5A shows a cross-sectional view of an example of a fixation structure with a retained ferrule portion and an associated header block that has a deformable structure that provides fixation to a medical lead within the header block upon the fixation structure causing compression of the deformable structure.

FIG. 5A shows a cross-sectional view of an example of a header block 500 with a design that utilizes a separate deformable structure for lead fixation. The header block 500 includes a housing 502, and within the housing 502 a bore 508 is defined by a nose structure 506 affixed or integral to the housing 502 and a series of interleaved seals 512 and electrical connectors 510. A proximal end of the lead 106 has been inserted into a bore 520 of a grip portion 504 and further into the bore 508 of the remainder of the header block 500. The electrical connectors 510 make physical contact with electrical contacts 522 of the lead 106 having lead body 528, and conductors 524 of the lead 106 are electrically coupled with corresponding electrical contacts 522 such that the conductors 524 are electrically coupled with the connectors 510. The conductors 524 extend to the distal end of the lead 106 (not shown in FIG. 5A) where they are electrically coupled to corresponding electrodes 108.

In this example, the lead 106 includes a ring 526 that has a flange that provides a hard stop for the lead 106 within the bore 508. Conventionally, a set screw would be tightened against this ring 526 to fix the position of the lead 106, but in this example the set screw has been eliminated. Instead, the nose structure 506 is provided with an engagement surface 516, which in this example is an exterior threaded surface, and the grip portion 504 is likewise provided with an interior threaded surface 514 that threads onto the surface 516. Therefore, the grip portion 504 in this example acts as a nut that tightens against the nose structure 506 when turned a given direction.

In this example, the fixation structure includes a retained ferrule portion 505, like that shown above in FIGS. 4A and 4B, that is positioned within the bore of the nose structure 506 and the lead 106 passes through the ferrule portion 505. The ferrule portion 505 has a flange 509 that is retained within a recess 507 of the grip portion 504 which is closed by the presence of a cap 503 joined to the grip portion 504. Movement of the grip portion 504 thereby forces the ferrule portion 505 to also move.

A deformable structure 518, which in this example is an elastomeric O-ring, is positioned between a blunt end of the ferrule portion 505 and an internal surface of the nose structure 506. As the grip portion 504 is manipulated by being turned in the tightening direction, the grip portion 504 moves toward the nose structure 506 and therefore moves the ferrule portion 505 toward the deformable structure 516 to compress the deformable structure 518. The deformable structure 518 then deforms to shrink in the direction of movement of the grip portion 504 but to grow in a direction perpendicular to the direction of movement of the grip portion 504 which is a radial direction of the bore 508. Because the blunt end of the grip portion 504 is turning but is against the ferrule portion 505 which is able to resist turning because of the clearance within the recess 507, there is less likelihood of the ferrule portion 505 turning against the deformable structure 518. This reduces the likelihood of any damage to the deformable structure 518.

By growing in the radial direction of the bore 508, the deformable structure 518 creates a force in that radial direction by pressing against the lead 106. In this example, the deformable structure 518 presses against the metal ring 526 of the lead 106, but it will be appreciated that the deformable structure 518 may be positioned to contact the lead body directly instead. This force against the lead 106 creates a high degree of friction between the deformable structure 518 and the ring 526 which provides fixation of the lead 106 within the header block 500. Additionally, the pressure of the deformable structure against the lead 106 presents a seal to restrict fluid ingress.

The grip portion 504 may have a collar as shown that eventually abuts the blunt end of the nose structure 506 to act as a stop. The deformable structure 518 will be creating pressure against the lead 106 at level adequate to fix the lead 106 position within the header block 500 just prior to the collar of the grip portion 504 reaching the nose structure 506. By having the collar of the grip portion 504 contact the nose structure 506, over compression of the deformable structure 518 that might cause damage is prevented.

Figure 5B:
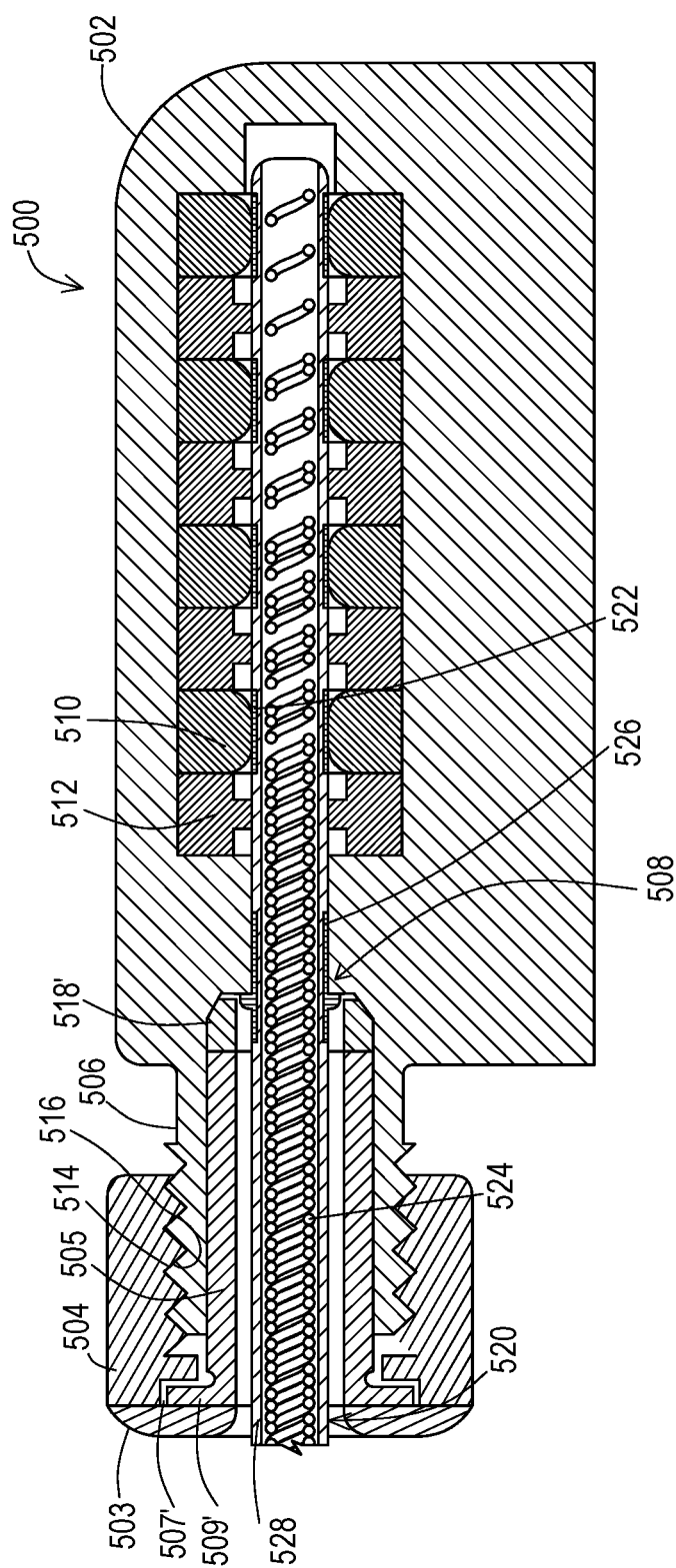
FIG. 5B shows a cross-sectional view of another example of a fixation structure and an associated header block that has a deformable structure that provides fixation to a medical lead within the header block upon the fixation structure causing compression of the deformable structure.

FIG. 5B shows a cross-sectional view of another example where the header block 500 and most components may be the same as from the example in FIG. 5A. However, rather than utilizing a separate deformable structure 518 of FIG. 5A that has the round or oval cross-section, a separate deformable structure 518' is utilized that has a conical cross-section. The internal surface of the housing 502 provides a matching conical surface to which the conical surface of the separate deformable structure 518' makes contact. As the ferrule portion 505 is forced against the separate deformable structure 518', the separate deformable structure 518' is forced to achieve a smaller inside diameter. This is similar to the deformable portion 305 of the fixation structure 300 of FIGS. 3A-3D except that this deformable conical structure 518' is separate from the fixation structure and may instead be retained within the bore of the header block 500.

The decreased inner diameter of the separate deformable structure 518' results in the deformable structure 518' making contact with the lead 106, and in this example, contacting the ring 526. This contact creates the lead fixation. The deformable structure 518' may be of various forms such as a metallic O-ring. This metallic O-ring may be coated or electroplated to allow better adhesion and to provide a ductile surface for better sealing against the lead body. As discussed above for the example of FIG. 5A, the grip portion 504 may have a collar that eventually abuts the blunt end of the nose structure to prevent over compression of the separate deformable structure 518'.

The housing 502 of FIGS. 5A and 5B may be constructed of various materials including those used for the fixation structure. For instance, the housing 502 may be constructed titanium, niobium, titanium-niobium alloys, MP35N® alloy (Ni—Co—Cr—Mo alloy), stainless steel and the like as well as other materials including rigid polymers that are biocompatible.

Figure 6A:
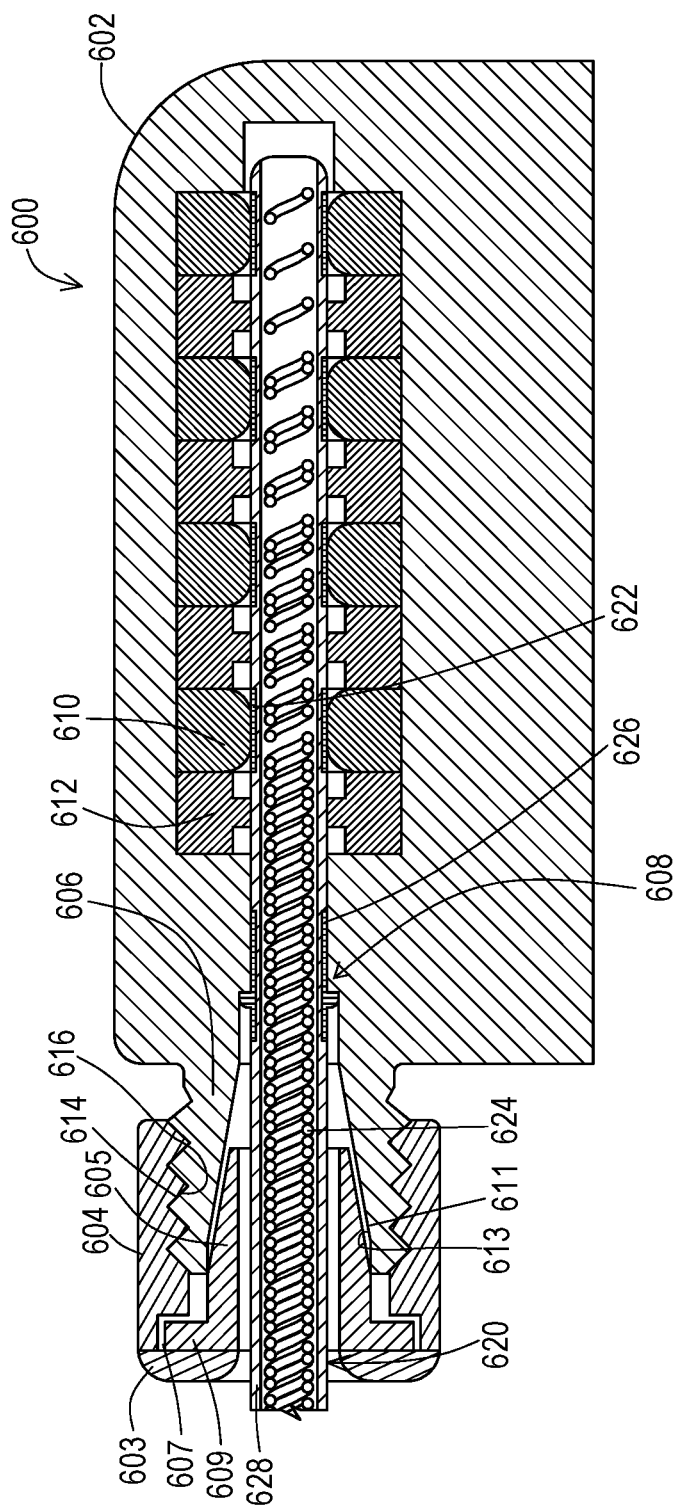
FIG. 6A shows a cross-sectional view of an example of a fixation structure and an associated header block where the fixation structure includes a retained deformable portion that provides fixation to a medical lead within the header block.

FIG. 6A shows a cross-sectional view of an example of a header block 600 that relies on the fixation structure having a retained deformable portion 605 for lead fixation. The header block 600 includes a housing 602, and within the housing 602 a bore 608 is defined by a nose structure 606 affixed or integral to the housing 602 and a series of interleaved seals 612 and electrical connectors 610. A proximal end of the lead 106 has been inserted into a bore 620 of a grip portion 604 and further into the bore 608 of the remainder of the header block 600. The electrical connectors 610 make physical contact with electrical contacts 622 of the lead 106, and conductors 624 of the lead 106 are electrically coupled with corresponding electrical contacts 622 such that the conductors 624 are electrically coupled with the connectors 610. The conductors 624 extend to the distal end of the lead 106 (not shown in FIG. 6A) where they are electrically coupled to corresponding electrodes 108.

In this example, the lead 106 includes a ring 626 that has a flange that provides a hard stop for the lead 106 within the bore 608. Conventionally, a set screw would be tightened against this ring 626 to fix the position of the lead 106, but in this example the set screw has been eliminated. Instead, the nose structure 606 is provided with an engagement surface 616, which in this example is an exterior threaded surface, and the grip portion 604 is likewise provided with an interior threaded surface 614 that threads onto the surface 616. Therefore, the grip portion 604 in this example acts as a nut that tightens against the nose structure 606 when turned a given direction.

In this example, the deformable portion 605 that includes the conical portion is positioned within the conical bore 611 of the nose structure 606 and the lead 106 passes through the deformable portion 605. The deformable portion 605 has a flange 609 that is retained within a recess 607 of the grip portion 604 and retained by the presence of the cap 603 joined to the grip portion 604. Movement of the grip portion 604 forces the deformable portion 605 to also move. Because the conical bore 611 of the nose structure 606 engages a conical surface 613 of the deformable portion 605, as the deformable portion 605 moves, the conical portion of the deformable portion 605 begins to deform where a diameter of the conical portion of the deformable portion 605 begins the decrease.

As the diameter of the bore through the conical portion of the deformable portion 605 decreases, the conical portion of the deformable portion 605 begins to compress onto the lead 106. In this example, the conical portion of the deformable portion 605 presses directly against a lead body 628 of the lead 106. This force against the lead 106 creates a high degree of friction between the deformable portion 605 and the lead body 628 which provides fixation of the lead 106 within the header block 600. Because the deformable portion 605 presents a relatively large amount of surface area in contact with the lead body 628 compared with an O-ring of the prior embodiments, the force is distributed over a relatively large surface area of the lead body 628 which lessens the likelihood of such pressure cause damage to the lead body 628.

Figure 6B:
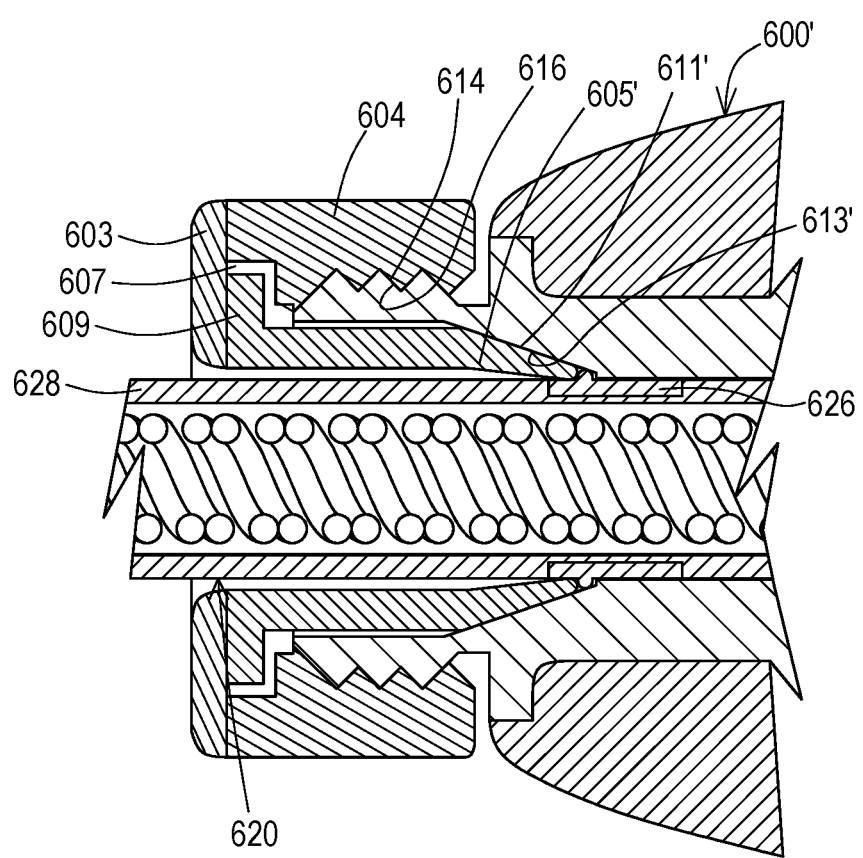
FIG. 6B shows a cross-sectional view of the example of FIG. 6A where a grip portion of the fixation structure has forced the deformable portion to compress into contact with the lead to provide the fixation.

FIG. 6B shows a header block 600' that includes a conical surface 613' where the slope of the conical surface 613' extends down to the point where the ring 626 is present. Thus, as the grip portion 604 is moved toward the header block 600' such as by turning the grip portion 604, the slope of the conical portion of the deformable portion 605' engages the slope of the conical surface 613' thereby causing the conical portion of the deformable portion 605' to be forced toward and eventually contact the ring 626. This contact against the ring 626, which is typically a rigid material such as a biocompatible metal, provides fixation of the lead 628 within the header block 600' without the conical portion of the deformable portion 605' contacting the lead body that is typically a polymer that is softer than the ring 626.

In these prior examples, the grip portion of the fixation structure has been described as providing a function like a nut by being threaded onto matching threads on the nose structure. However, other forms of the grip portion are also possible for these various examples that may or may not include threads. Likewise, the nose structure of these examples may or may not utilize threads. For instance, the grip portion could have other structures that lock to structures of the nose structure upon a clinician manipulating the grip portion by forcing the grip portion to move toward the nose structure, which in turn causes the deformation of the deformable portion of the fixation structure that creates contact with the lead to provide fixation of the lead within the header block.

Other modifications are also possible. For example, the header blocks 500 and 600 discussed above are shown as having a single lead bore and therefore a single lead fixation configuration of the fixation structure including the grip portion and the retained ferrule portion or retained deformable portion. However, it will be appreciated that header blocks 500 and 600 may be provided with multiple lead bores where a grip and deformable structure is provided for each bore so that each lead may be individually fixed in place and removed by manipulation of the corresponding grip.

To ensure that grip portion in the several preceding examples maintains a tightened position to maintain fixation to the medical lead, mating structures such as holes and a detent may be provided on the grip portion and on the header block, respectively. Once the grip portion is tightened, a detent engages a particular hole which prevents the grip portion from turning during normal use but may be turned when force is being applied by a user. While a single detent may be used, it will be appreciated that multiple detents may be present and may be spaced in correspondence with the spacing of the corresponding holes. Additionally, the position of the detent(s) and the holes may instead be swapped where the detent(s) are present on the radial surface of the grip portion while the holes are present on the nose structure.

Figure 7:
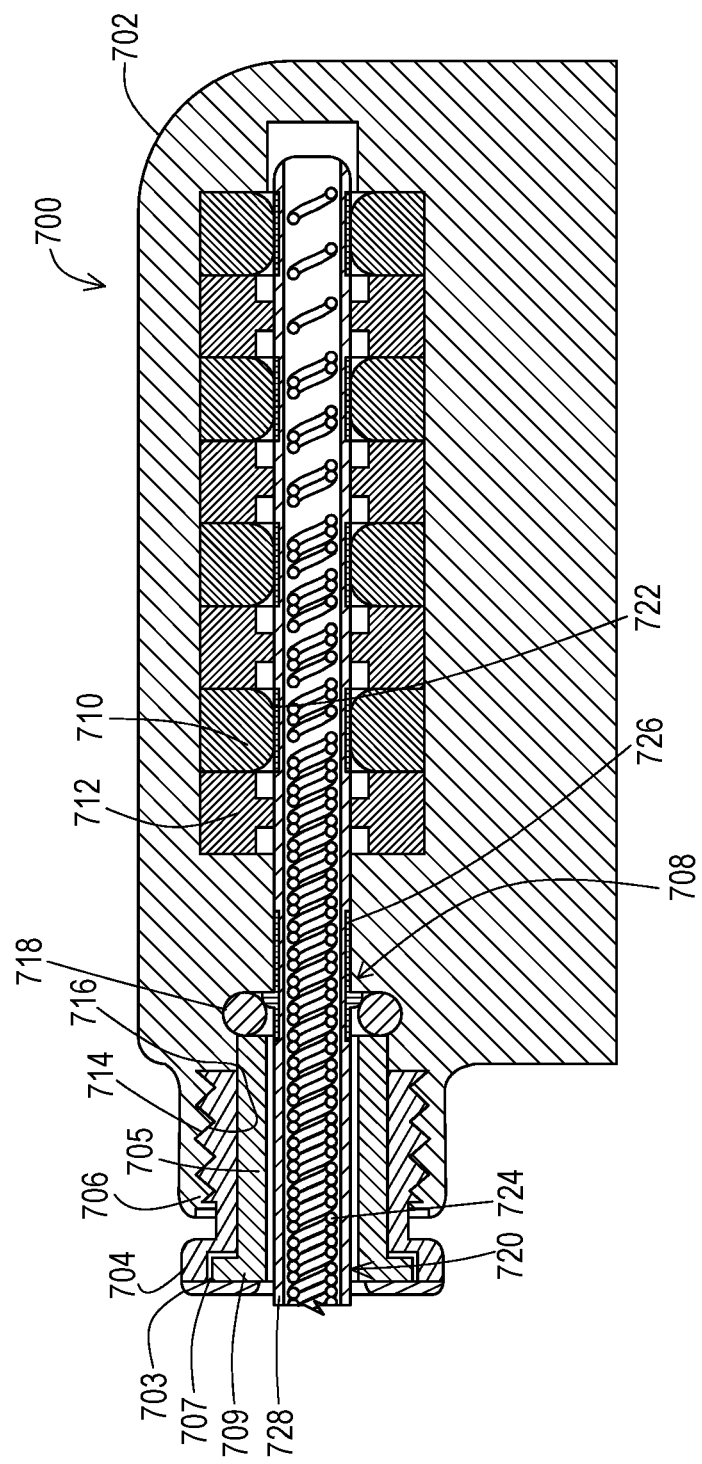
FIG. 7 shows a cross-sectional view of another example of a fixation structure with a retained ferrule portion and an associated header block that has a deformable structure that provides fixation to a medical lead within the header block upon the fixation structure causing compression of the deformable structure.

FIG. 7 shows a cross-sectional view of a second example of a header block 700 with a design that utilizes a fixation structure and a separate deformable structure for lead fixation. The fixation structure includes a grip portion 704, a cap 703 attached to the grip portion to define a recess 707, and a ferrule portion 705 with a flange 709 retained within the recess 707. The header block 700 includes a housing 702, and within the housing 702 a bore 708 is defined by a nose structure 706 affixed or integral to the housing 702 and a series of interleaved seals 712 and electrical connectors 710. A proximal end of the lead 106 having lead body 728 has been inserted into a bore 720 of a grip portion 704 of the fixation structure and further into the bore 708 of the remainder of the header block 700. The electrical connectors 710 make physical contact with electrical contacts 722 of the lead 106, and conductors 724 of the lead 106 are electrically coupled with corresponding electrical contacts 722 such that the conductors 724 are electrically coupled with the connectors 710. The conductors 724 extend to the distal end of the lead 106 (not shown in FIG. 7) where they are electrically coupled to corresponding electrodes 108.

In this example, the lead 106 includes a ring 726 that has a flange that provides a hard stop for the lead 106 within the bore 708. The nose structure 706 is provided with an engagement surface 714, which in this example is an interior threaded surface, and the grip portion 704 is likewise provided with an exterior threaded surface 716 that threads onto the surface 714. Therefore, the grip portion 704 in this example tightens against the nose structure 706 when turned a given direction.

A deformable structure 718, which in this example is also an elastomeric O-ring, is positioned between a blunt end of the ferrule portion 705 and an internal surface of the nose structure 706. As the grip portion 704 is manipulated by being turned in the tightening direction, the retained ferrule portion 705 moves toward the nose structure 706 and therefore compresses the deformable structure 718. The deformable structure 718 then deforms to shrink in the direction of movement of the ferrule portion 705 but to grow in a direction perpendicular to the direction of movement of the ferrule portion 705 which is a radial direction of the bore 708.

By growing in the radial direction of the bore 708, the deformable structure 718 creates a force in that radial direction by pressing against the lead 106. In this example, the deformable structure 718 presses against the metal ring 726 of the lead 106, but it will be appreciated that the deformable structure 718 may be positioned to contact the lead body directly instead. This force against the lead 106 creates a high degree of friction between the deformable structure 718 and the ring 726 which provides fixation of the lead 106 within the header block 700. Additionally, the pressure of the deformable structure against the lead 106 presents a seal to restrict fluid ingress.

Figure 8:
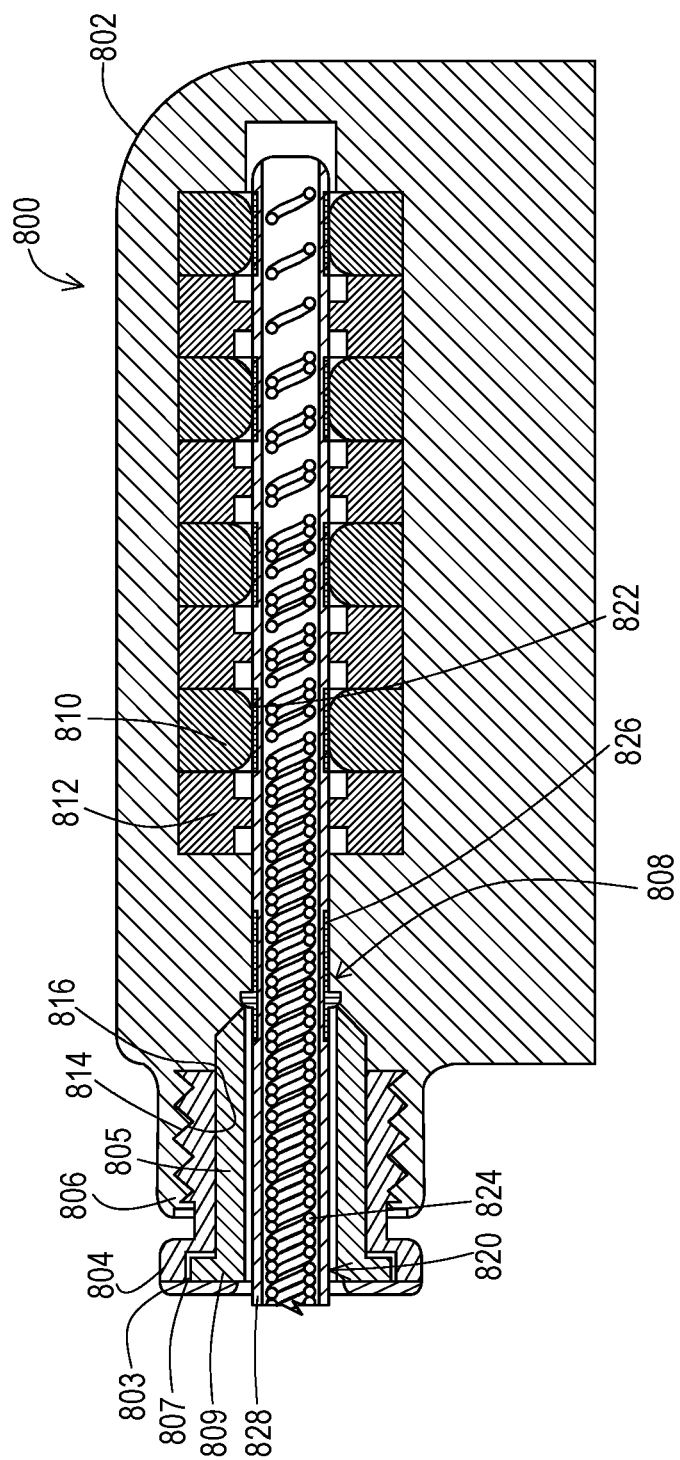
FIG. 8 shows a cross-sectional view of another example of a fixation structure and an associated header block where the fixation structure includes a retained deformable portion that provides fixation to a medical lead within the header block.

FIG. 8 shows a cross-sectional view of another example of a header block 800 with a design that utilizes a retained deformable portion 805 of a fixation structure for lead fixation. The fixation structure includes a grip portion 804, a cap 803 attached to the grip portion to define a recess 807, and a deformable portion 805 with a flange 809 retained within the recess 807. The header block 800 includes a housing 802, and within the housing 802 a bore 808 is defined by a nose structure 806 affixed or integral to the housing 802 and a series of interleaved seals 812 and electrical connectors 810. A proximal end of the lead 106 having lead body 828 has been inserted into a bore 820 of the grip portion 804 of the fixation structure. The electrical connectors 810 make physical contact with electrical contacts 822 of the lead 106, and conductors 824 of the lead 106 are electrically coupled with corresponding electrical contacts 822 such that the conductors 824 are electrically coupled with the connectors 810. The conductors 824 extend to the distal end of the lead 106 (not shown in FIG. 8) where they are electrically coupled to corresponding electrodes 108.

In this example, the lead 106 includes a ring 826 that has a flange that provides a hard stop for the lead 106 within the bore 808. The nose structure 806 is provided with an engagement surface 814, which in this example is an interior threaded surface, and the grip portion 804 is likewise provided with an exterior threaded surface 816 that threads onto the surface 814. Therefore, the grip portion 804 in this example tightens against the nose structure 806 when turned a given direction.

The deformable portion 805 moved further into the bore as the grip portion 804 is tightened so that the deformable portion 805 engages an internal surface of the nose structure 806. As the grip portion 804 is manipulated by being further turned in the tightening direction, the deformable portion 805 then compresses in the radial direction of the bore 808 to create a force in that radial direction by pressing against the lead 106. In this example, the deformable portion 805 presses against the metal ring 826 of the lead 106, but it will be appreciated that the deformable portion 805 may be positioned to contact the lead body directly instead. This force against the lead 106 creates a high degree of friction between the deformable portion 805 and the ring 826 which provides fixation of the lead 106 within the header block 800.

Figure 9A:
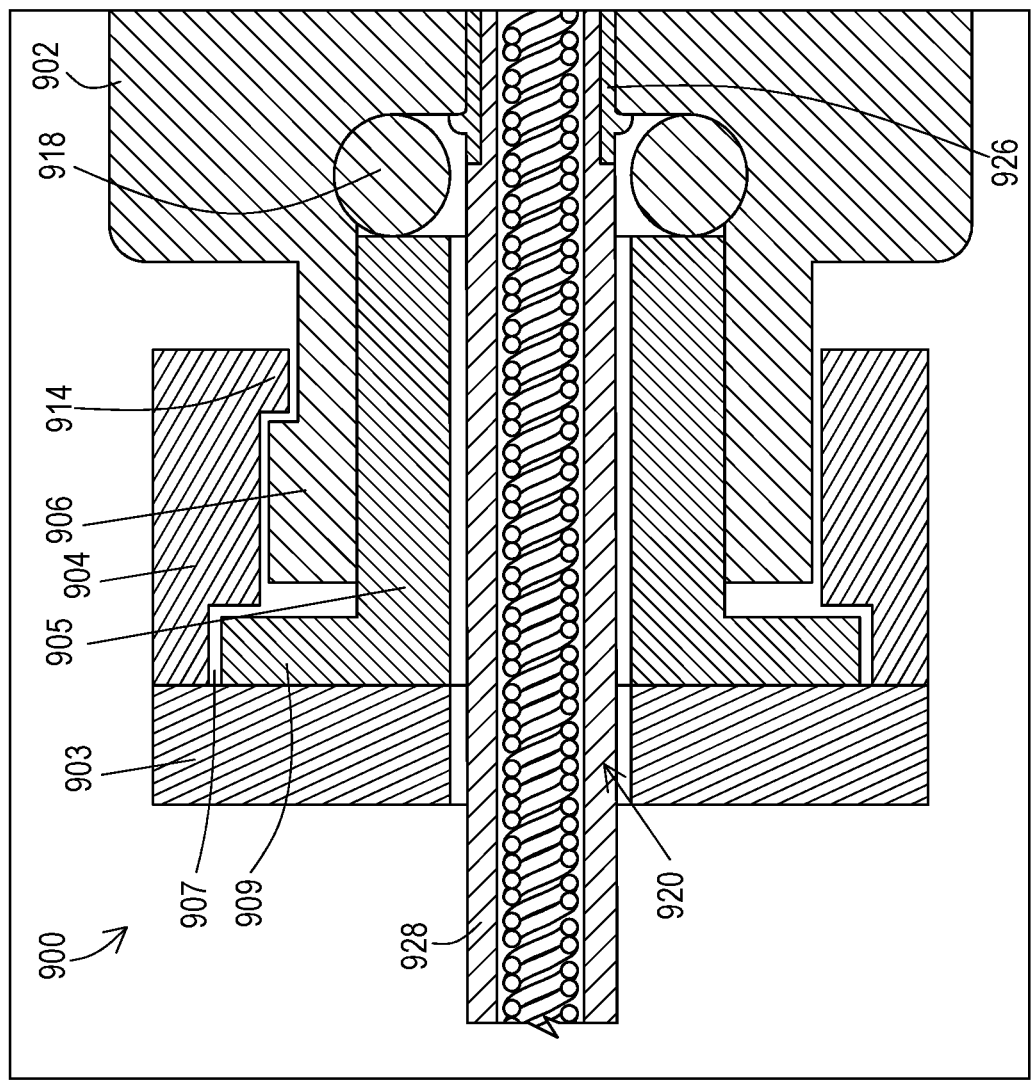
FIG. 9A shows a cross-sectional view of an example of a fixation structure that includes a retained ferrule and that utilizes a twist lock to secure the position of the grip portion and thereby maintain fixation of a medical lead.
Figure 9B:
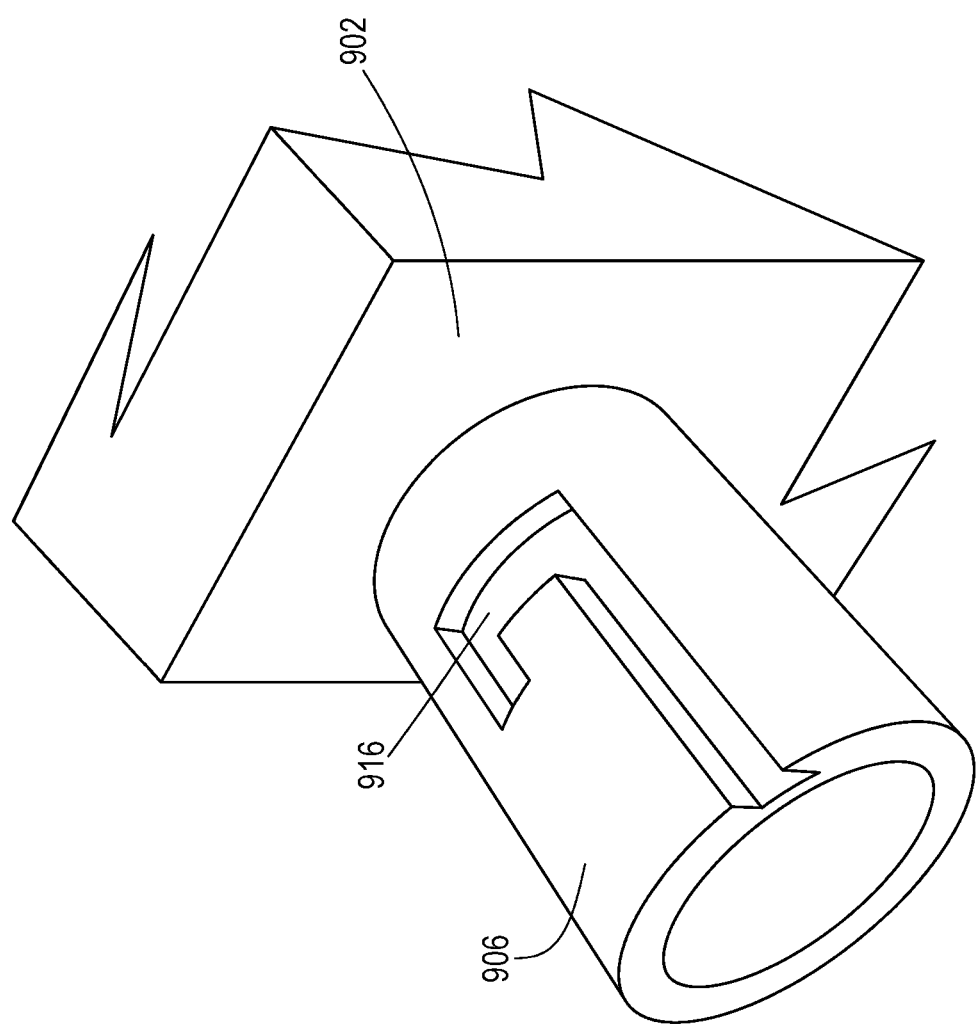
FIG. 9B shows a perspective view of the medical device of the example of FIG. 9A to further illustrate a slot that provides the twist lock in conjunction with the grip portion.

FIGS. 9A and 9B show an example where a twist locking grip portion is used for the fixation structure instead of a threaded grip portion. The housing 902 of the header block 900 of a medical device includes the deformable structure 918 that engages the lead 928, such as at the connector 926 to provide fixation. The fixation structure includes a grip portion 904 and retained ferrule portion 905. A flange 909 of the ferrule portion 905 rests within a recess 907 of the grip portion 904 and a cap 903 retains the flange 909.

The translation of the grip portion 904 due to force by a user causes translation of the ferrule portion 905 which is forced into the deformable structure 918 to cause compression onto the lead 928 that passes through the bore 920. Rather than threading the grip portion 904 onto the nose structure 906, the grip portion 904 includes a protrusion 914 that engages and travels along a slot 916 present on the nose structure 906. As can be seen in FIG. 9B, the slot 916 has a turn that establishes a locked position when the protrusion 914 is forced as far as possible toward the housing 902, is then twisted as far as possible within the slot 916, and is thereafter released. There is a slight amount of over pressure applied to the deformable structure 918 during the twisting motion and then the pressure is reduced slightly to the normal lead fixation pressure once the grip portion 904 is released into the locked position provided by the turn in the path of slot the 916.

While the twist of the grip portion 904 to the locked position in the path of the slot 916 is a counter-clockwise twist as shown in FIG. 9B, it will be appreciated that the path of the slot 916 could instead provide for a clockwise twist to lock the position of the grip portion 904. Additionally, the provide additional back pressure on the grip portion 904 to further hold the grip portion 904 in the locked position provided by the path of the slot 916, a washer may be positioned between the header block 900 and the grip portion 904. This washer may be a lock washer, a Bellevue washer, and the like to provide the back pressure onto the grip portion 904. Additionally, the washer may be attached to the grip portion 904, attached to the header block 900, or may exist as a separate object positioned between the grip portion 904 and header block 900. Furthermore, it will be appreciated that such a washer may be included in the prior embodiments also in order to create pressure and friction against the threaded grip portions in order to resist the loosening of the grip portions.

Figure 10:
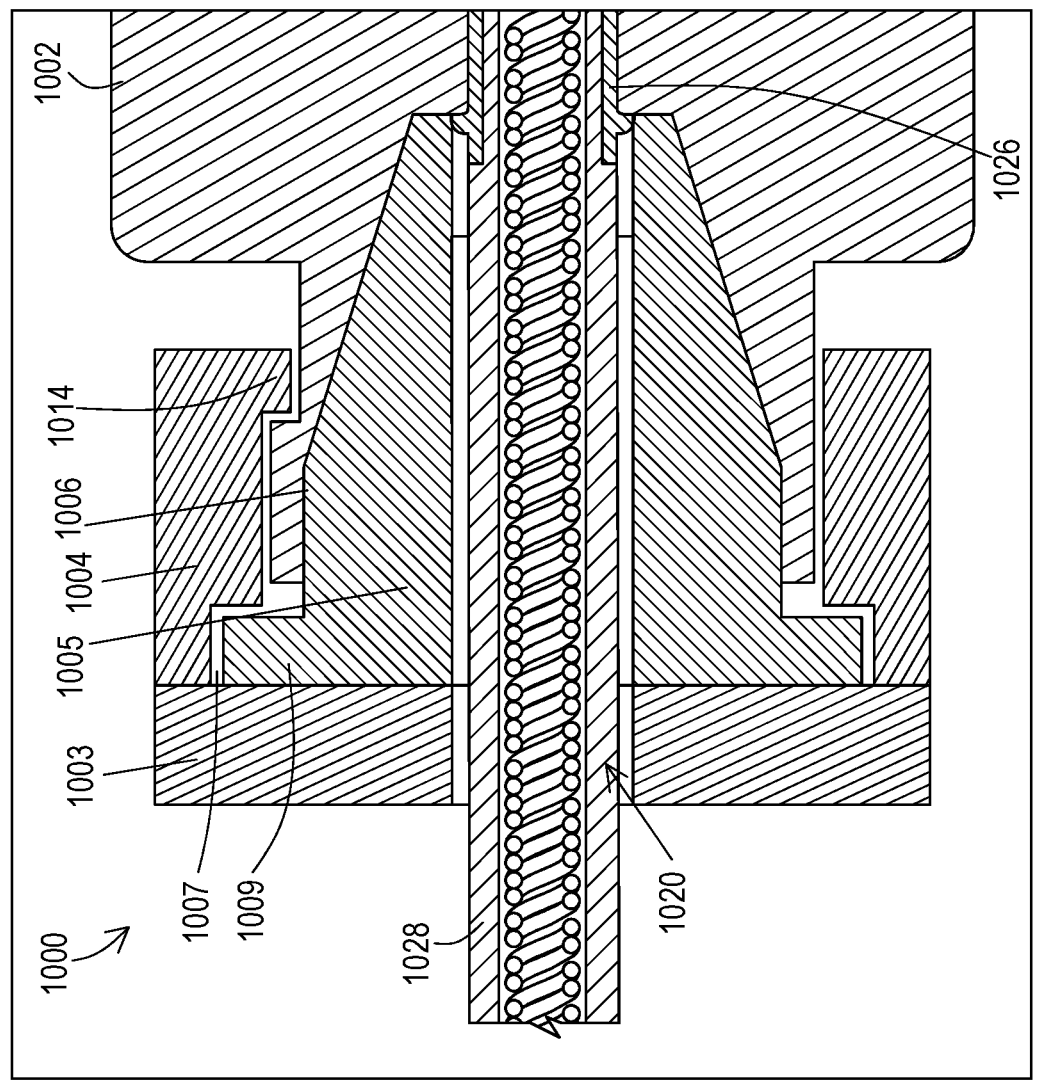
FIG. 10 shows a cross-sectional view of an example of a fixation structure that includes a retained deformable portion and that utilizes a twist lock to secure the position of the grip portion relative to a medical device with a twist lock slot as shown in FIGS. 9A and 9B and thereby maintains fixation of a medical lead.

FIG. 10 shows another example where a twist locking grip portion is used for the fixation structure instead of a threaded grip portion. The housing 1002 of the header block 1000 of a medical device receives a retained deformable portion 1005 of a fixation structure that also includes a grip portion 1004. A flange 1009 of the deformable portion 1005 rests in a recess 1007 of the grip portion 1004 and is retained by the presence of a cap 1003 joined to the grip portion 1004.

The translation of the grip portion 1004 due to force by a user causes translation of the deformable portion 1005 which is forced into the conical portion of the bore of the header block 1000 to cause compression of a conical portion of the deformable portion 1005 onto the lead 1028 that passes through the bore 1020. In this example, the deformable portion 1005 engages the lead 1028 at a connector 1026 to provide fixation. Rather than threading the grip portion 1004 onto the nose structure 1006, the grip portion 1004 includes a protrusion 1014 that engages and travels along a slot, such as the slot 916 of FIG. 9B, that is present on the nose structure 1006 so that the grip portion 1004 is locked into position in the same manner described above for the grip portion 904 of FIG. 9A.

Figure 11:
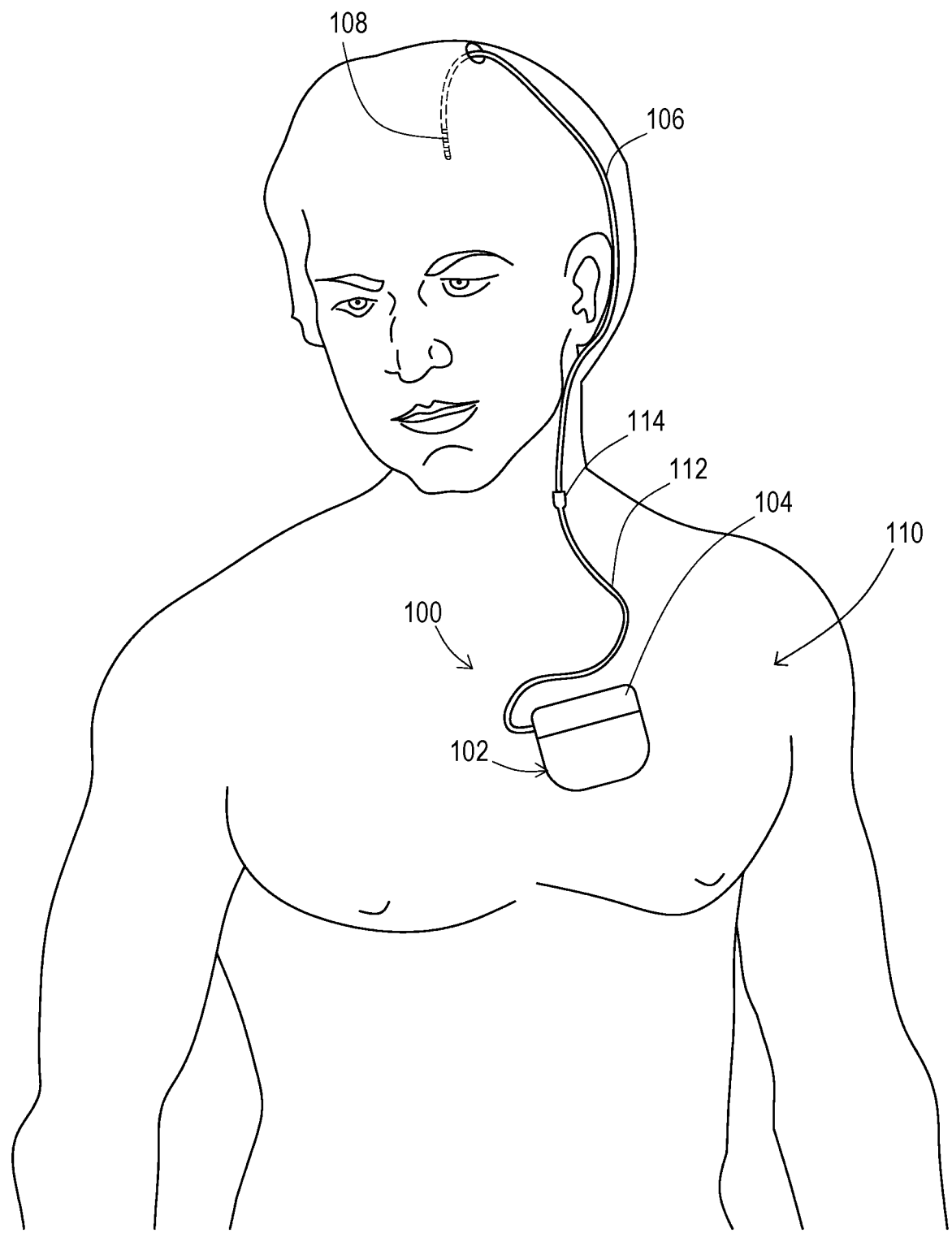
FIG. 11 shows an operating environment for various embodiments where a medical system including a medical device, a lead extension, and a medical lead are attached to or implanted into a patient.

FIG. 11 shows a medical system 100' that includes a medical device 102, a lead extension 112, and a medical lead 106. In this particular example, the medical system 100' including the medical device 102, the lead extension 112, and the medical lead 106 are implantable. The medical lead 106 includes a proximal end that has been inserted into a bore of a connector block 114 of the lead extension 112 while the lead extension 112 includes a proximal end that has been inserted into a bore of a header block 104 of the medical device 102. The distal end of the medical lead 106 includes electrodes 108 that are positioned at a target site where electrical stimulation therapy is to be provided. It will also be understood that the specific implant, lead extension, and lead location of FIG. 11 is to show an example and that the embodiments of the fixation structure apply to any implant, lead extension, and lead location.

Figure 12A:
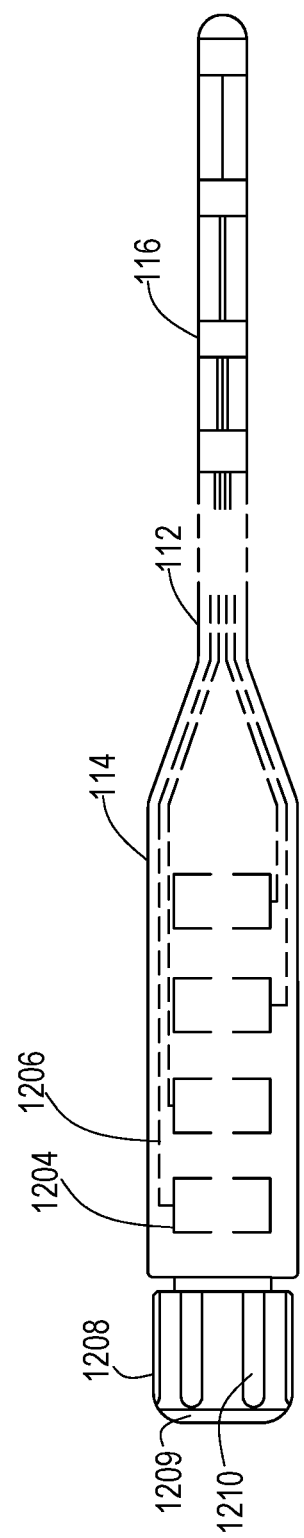
FIG. 12A shows an example of a lead extension having a fixation structure with a grip portion that can be manipulated to provide lead fixation.

FIG. 12A shows an example of the lead extension 112 and a connector block 114 of the lead extension 112. The lead extension 112 of this example includes conductors 1206 that provides electrical stimulation by connecting with contacts 116 of a proximal region of the body of the lead extension 112 and by connecting with corresponding electrical connectors 1204 inside of the connector block 114 on the distal region. The lead extension 112 of this example also includes a grip portion 1208 of a fixation structure, like that shown in FIGS. 3A-3D or FIGS. 4A-4B, that can be grasped and manipulated by a clinician, and thus by hand and without tools, when connecting a lead 106 to the connector block 114 of the lead extension 112.

Figure 12B:
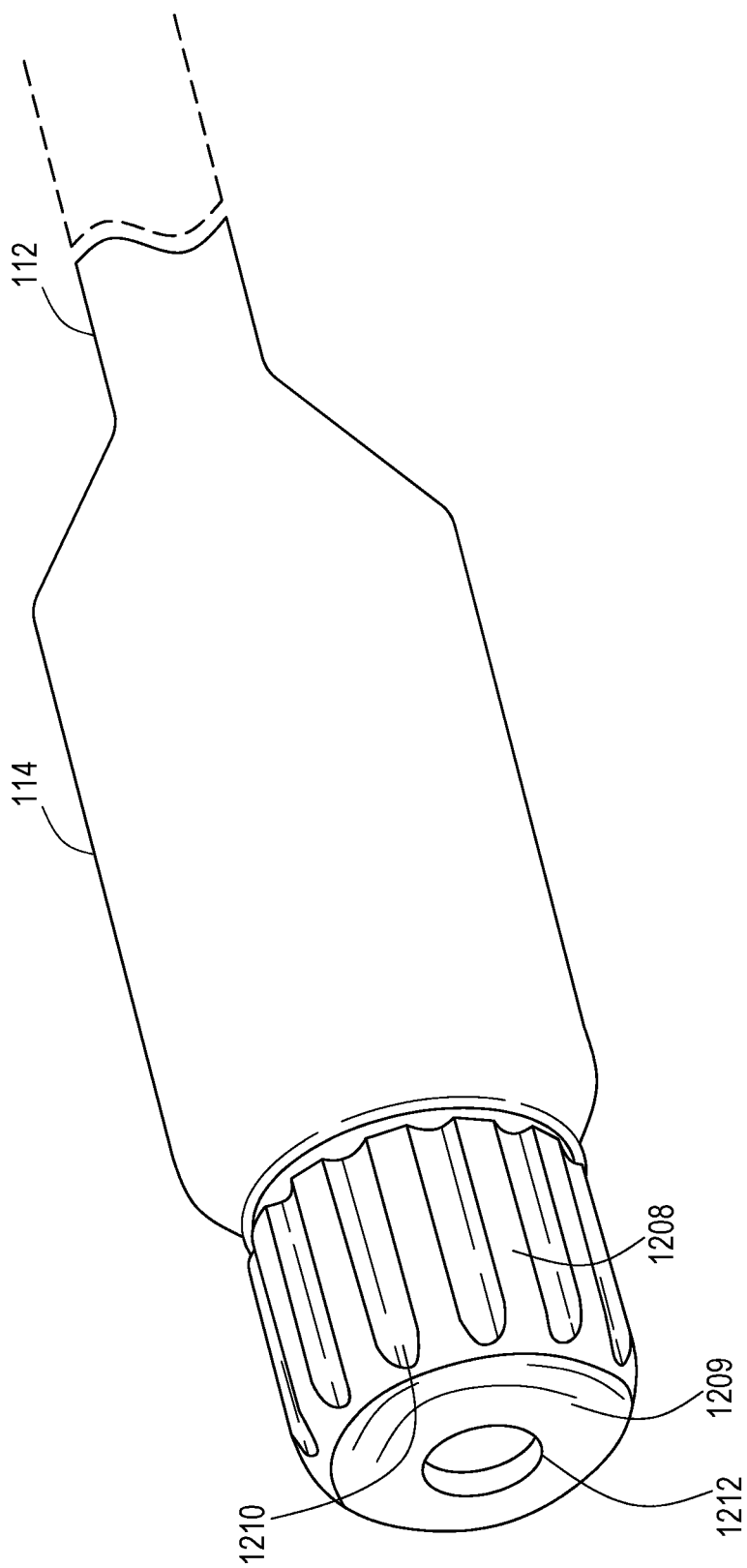
FIG. 12B shows a perspective view of a connector block and fixation structure of the lead extension.

The connector block 114 and grip portion 1208 are also shown in the perspective view of FIG. 12B. As can be seen in FIGS. 12A and 12B, the grip portion 1208 may include grooves 1210 or other knurled like surface treatments to provide additional friction that aids in grasping and manipulating the grip portion 1208. The grip portion 1208 is movable relative to the connector block 114 which allows the grip portion 1208 to be manipulated to provide fixation of the lead 106 that has been inserted into a bore 1212 of the grip portion 1208 and cap 1209 of this example that leads to the bore of the connector block 114.

Figure 13A:
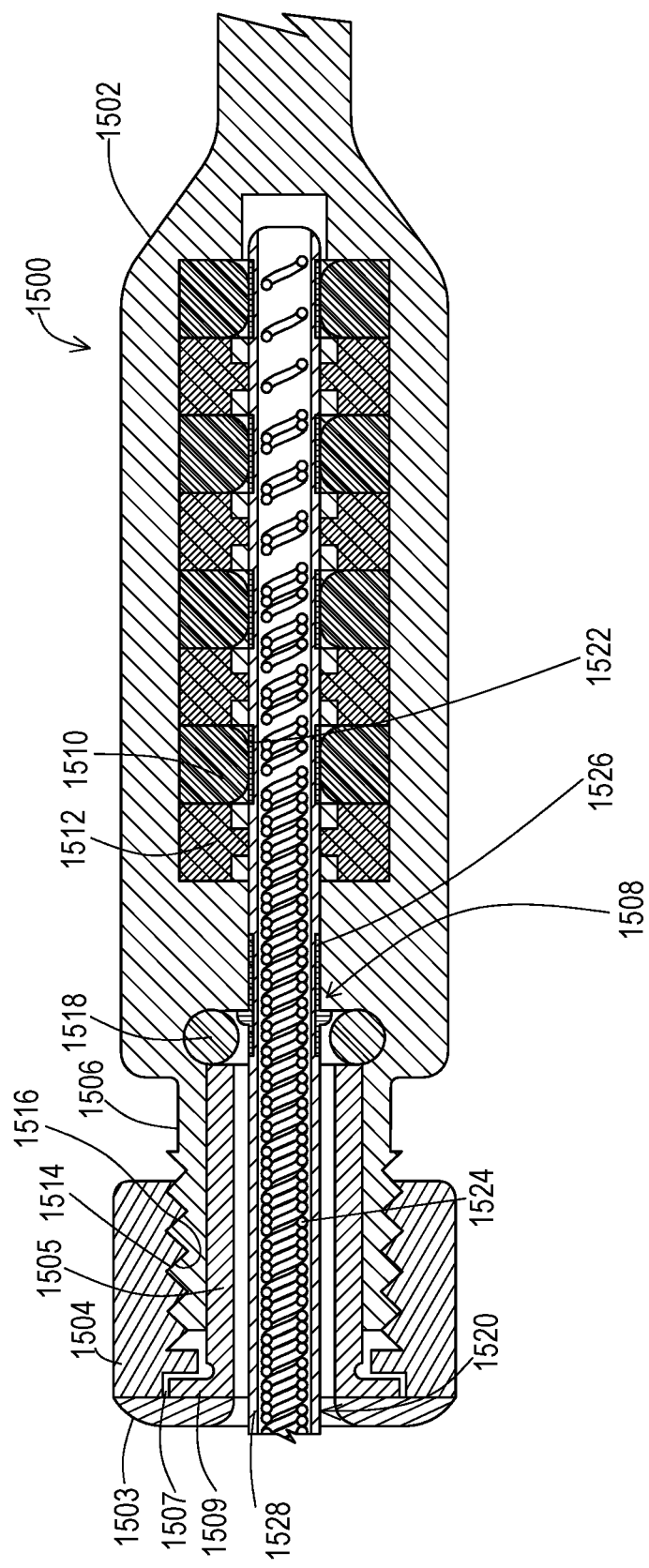
FIG. 13A shows a cross-sectional view of an example of a fixation structure with a retained ferrule portion and an associated connector block of a lead extension that has a deformable structure that provides fixation to a medical lead within the connector block upon the fixation structure causing compression of the deformable structure.

FIG. 13A shows a cross-sectional view of an example of a connector block 1500 with a design that utilizes a separate deformable structure for lead fixation. The connector block 1500 includes a housing 1502, and within the housing 1502 a bore 1508 is defined by a nose structure 1506 affixed or integral to the housing 1502 and a series of interleaved seals 1512 and electrical connectors 1510. A proximal end of the lead 106 has been inserted into a bore 1520 of a grip portion 1504 and further into the bore 1508 of the remainder of the connector block 1500. The electrical connectors 1510 make physical contact with electrical contacts 1522 of the lead 106 having lead body 1528, and conductors 1524 of the lead 106 are electrically coupled with corresponding electrical contacts 1522 such that the conductors 1524 are electrically coupled with the connectors 1510. The conductors 1524 extend to the distal end of the lead 106 (not shown in FIG. 13A) where they are electrically coupled to corresponding electrodes 108.

In this example, the lead 106 includes a ring 1526 that has a flange that provides a hard stop for the lead 106 within the bore 1508. Conventionally, a set screw would be tightened against this ring 1526 to fix the position of the lead 106, but in this example the set screw has been eliminated. Instead, the nose structure 1506 is provided with an engagement surface 1516, which in this example is an exterior threaded surface, and the grip portion 1504 is likewise provided with an interior threaded surface 1514 that threads onto the surface 1516. Therefore, the grip portion 1504 in this example acts as a nut that tightens against the nose structure 1506 when turned a given direction.

In this example, the fixation structure includes a retained ferrule portion 1505, like that shown above in FIGS. 4A and 4B, that is positioned within the bore of the nose structure 1506 and the lead 106 passes through the ferrule portion 1505. The ferrule portion 1505 has a flange 1509 that is retained within a recess 1507 of the grip portion 1504 which is closed by the presence of a cap 1503 joined to the grip portion 1504. Movement of the grip portion 1504 thereby forces the ferrule portion 1505 to also move.

A deformable structure 1518, which in this example is an elastomeric O-ring, is positioned between a blunt end of the ferrule portion 1505 and an internal surface of the nose structure 1506. As the grip portion 1504 is manipulated by being turned in the tightening direction, the grip portion 1504 moves toward the nose structure 1506 and therefore moves the ferrule portion 1505 toward the deformable structure 1516 to compress the deformable structure 1518. The deformable structure 1518 then deforms to shrink in the direction of movement of the grip portion 1504 but to grow in a direction perpendicular to the direction of movement of the grip portion 1504 which is a radial direction of the bore 1508. Because the blunt end of the grip portion 1504 is turning but is against the ferrule portion 1505 which is able to resist turning because of the clearance within the recess 1507, there is less likelihood of the ferrule portion 1505 turning against the deformable structure 1518. This reduces the likelihood of any damage to the deformable structure 1518.

By growing in the radial direction of the bore 1508, the deformable structure 1518 creates a force in that radial direction by pressing against the lead 106. In this example, the deformable structure 1518 presses against the metal ring 1526 of the lead 106, but it will be appreciated that the deformable structure 1518 may be positioned to contact the lead body directly instead. This force against the lead 106 creates a high degree of friction between the deformable structure 1518 and the ring 1526 which provides fixation of the lead 106 within the connector block 1500. Additionally, the pressure of the deformable structure against the lead 106 presents a seal to restrict fluid ingress.

The grip portion 1504 may have a collar as shown that eventually abuts the blunt end of the nose structure 1506 to act as a stop. The deformable structure 1518 will be creating pressure against the lead 106 at level adequate to fix the lead 106 position within the connector block 1500 just prior to the collar of the grip portion 1504 reaching the nose structure 1506. By having the collar of the grip portion 1504 contact the nose structure 1506, over compression of the deformable structure 1518 that might cause damage is prevented.

Figure 13B:
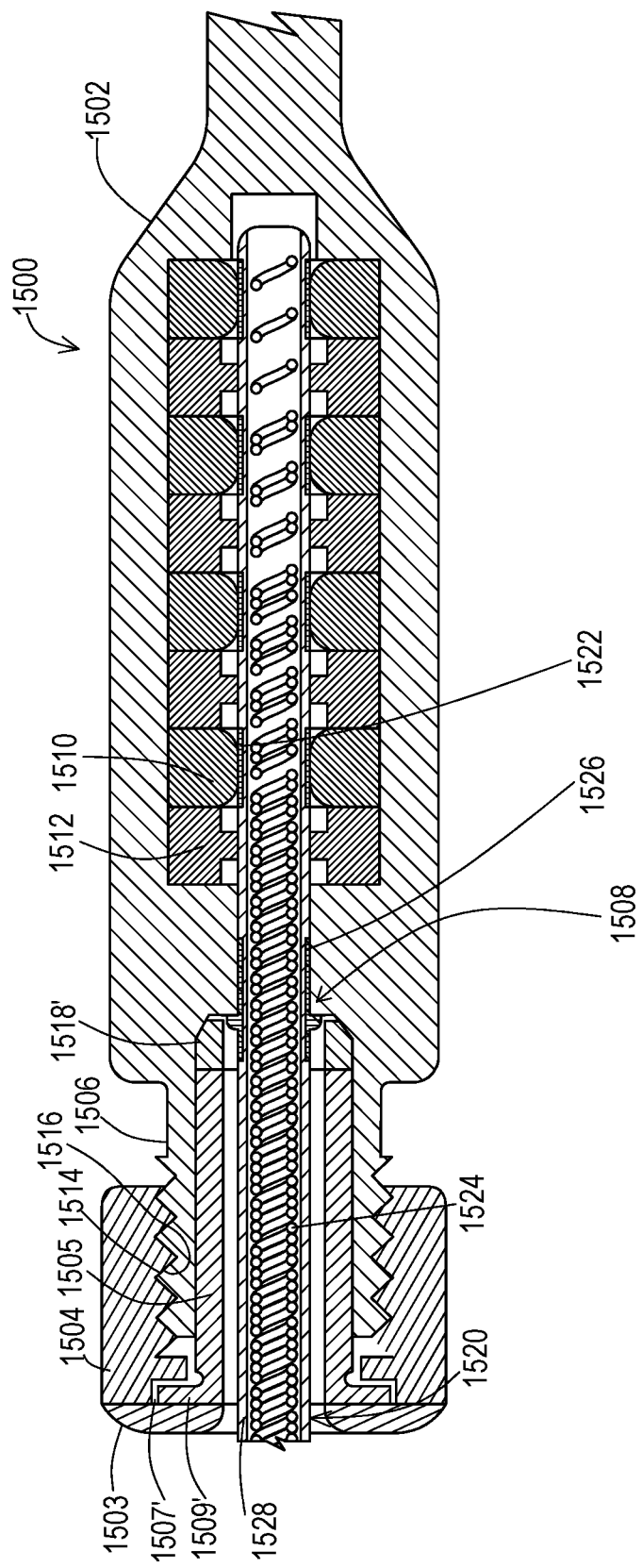
FIG. 13B shows a cross-sectional view of another example of a fixation structure and an associated connector block of a lead extension that has a deformable structure that provides fixation to a medical lead within the connector block upon the fixation structure causing compression of the deformable structure.

FIG. 13B shows a cross-sectional view of another example where the connector block 1500 and most components may be the same as from the example in FIG. 13A. However, rather than utilizing a separate deformable structure 1518 of FIG. 13A that has the round or oval cross-section, a separate deformable structure 1518' is utilized that has a conical cross-section. The internal surface of the housing 1502 provides a matching conical surface to which the conical surface of the separate deformable structure 1518' makes contact. As the ferrule portion 1505 is forced against the separate deformable structure 1518', the separate deformable structure 1518' is forced to achieve a smaller inside diameter. This is similar to the deformable portion 305 of the fixation structure 300 of FIGS. 3A-3D except that this deformable conical structure 1518' is separate from the fixation structure and may instead be retained within the bore of the connector block 1500.

The decreased inner diameter of the separate deformable structure 1518' results in the deformable structure 1518' making contact with the lead 106, and in this example, contacting the ring 1526. This contact creates the lead fixation. The deformable structure 1518' may be of various forms such as a metallic O-ring. This metallic O-ring may be coated or electroplated to allow better adhesion and to provide a ductile surface for better sealing against the lead body. As discussed above for the example of FIG. 13A, the grip portion 1504 may have a collar that eventually abuts the blunt end of the nose structure to prevent over compression of the separate deformable structure 1518'.

The housing 1502 of FIGS. 13A and 13B may be constructed of various materials including those used for the fixation structure. For instance, the housing 1502 may be constructed of titanium, niobium, titanium-niobium alloys, MP35N® alloy (Ni—Co—Cr—Mo alloy), stainless steel and the like as well as other materials including rigid polymers that are biocompatible.

Figure 14A:
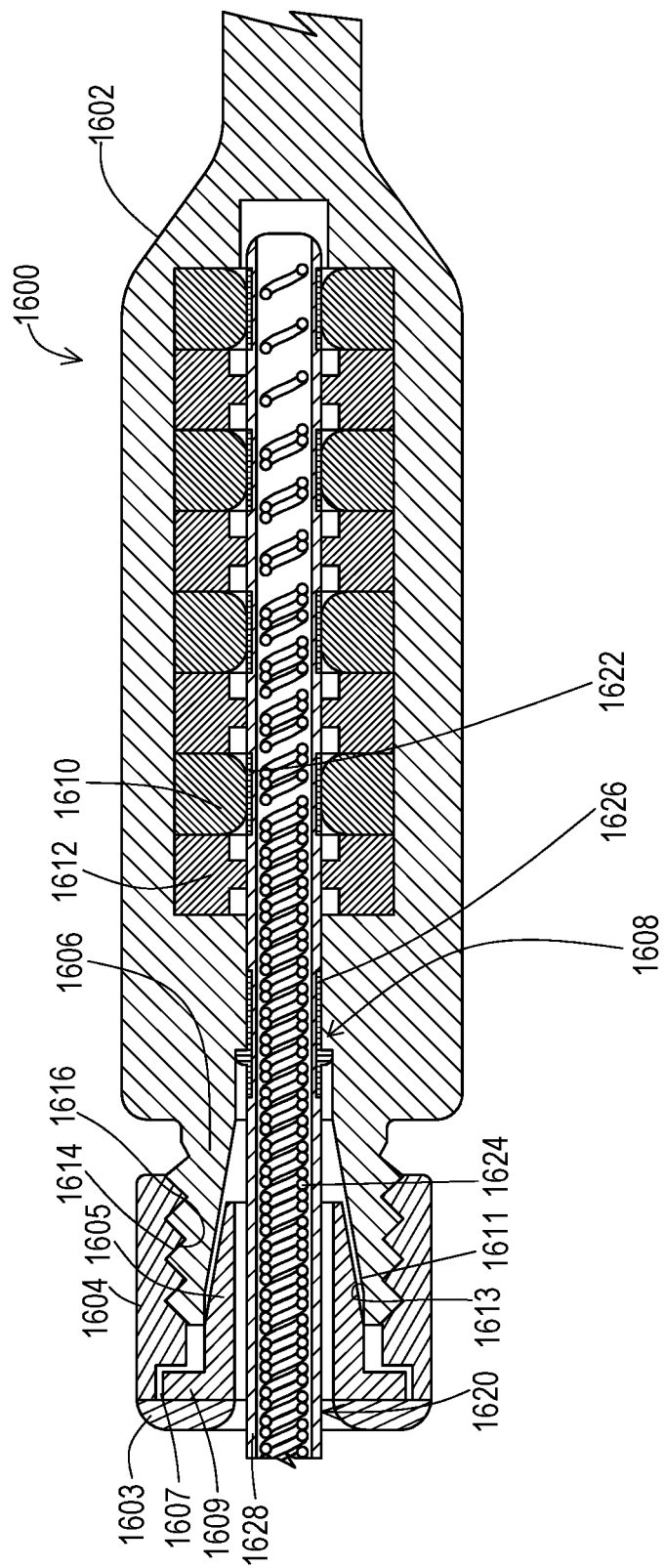
FIG. 14A shows a cross-sectional view of an example of a fixation structure and an associated connector block of a lead extension where the fixation structure includes a retained deformable portion that provides fixation to a medical lead within the connector block.

FIG. 14A shows a cross-sectional view of an example of a connector block 1600 that relies on the fixation structure having a retained deformable portion 1605 for lead fixation. The connector block 1600 includes a housing 1602, and within the housing 1602 a bore 1608 is defined by a nose structure 1606 affixed or integral to the housing 1602 and a series of interleaved seals 1612 and electrical connectors 1610. A proximal end of the lead 106 has been inserted into a bore 1620 of a grip portion 1604 and further into the bore 1608 of the remainder of the connector block 1600. The electrical connectors 1610 make physical contact with electrical contacts 1622 of the lead 106, and conductors 1624 of the lead 106 are electrically coupled with corresponding electrical contacts 1622 such that the conductors 1624 are electrically coupled with the connectors 1610. The conductors 1624 extend to the distal end of the lead 106 (not shown in FIG. 14A) where they are electrically coupled to corresponding electrodes 108.

In this example, the lead 106 includes a ring 1626 that has a flange that provides a hard stop for the lead 106 within the bore 1608. Conventionally, a set screw would be tightened against this ring 1626 to fix the position of the lead 106, but in this example the set screw has been eliminated. Instead, the nose structure 1606 is provided with an engagement surface 1616, which in this example is an exterior threaded surface, and the grip portion 1604 is likewise provided with an interior threaded surface 1614 that threads onto the surface 1616. Therefore, the grip portion 1604 in this example acts as a nut that tightens against the nose structure 1606 when turned a given direction.

In this example, the deformable portion 1605 that includes the conical portion is positioned within the conical bore 1611 of the nose structure 1606 and the lead 106 passes through the deformable portion 1605. The deformable portion 1605 has a flange 1609 that is retained within a recess 1607 of the grip portion 1604 and retained by the presence of the cap 1603 joined to the grip portion 1604. Movement of the grip portion 1604 forces the deformable portion 1605 to also move. Because the conical bore 1611 of the nose structure 1606 engages a conical surface 1613 of the deformable portion 1605, as the deformable portion 1605 moves, the conical portion of the deformable portion 1605 begins to deform where a diameter of the conical portion of the deformable portion 1605 begins the decrease.

As the diameter of the bore through the conical portion of the deformable portion 1605 decreases, the conical portion of the deformable portion 1605 begins to compress onto the lead 106. In this example, the conical portion of the deformable portion 1605 presses directly against a lead body 1628 of the lead 106. This force against the lead 106 creates a high degree of friction between the deformable portion 1605 and the lead body 1628 which provides fixation of the lead 106 within the connector block 1600. Because the deformable portion 1605 presents a relatively large amount of surface area in contact with the lead body 1628 compared with an O-ring of the prior embodiments, the force is distributed over a relatively large surface area of the lead body 1628 which lessens the likelihood of such pressure cause damage to the lead body 1628.

Figure 14B:
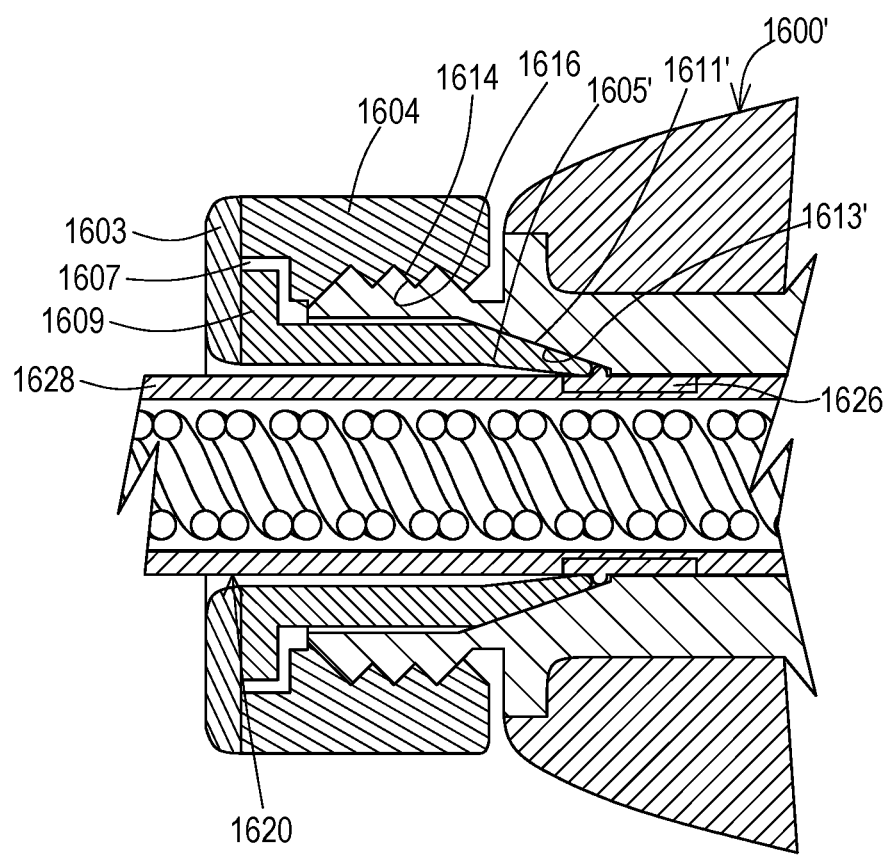
FIG. 14B shows a cross-sectional view of the example of FIG. 6A where a grip portion of the fixation structure has forced the deformable portion to compress into contact with the lead to provide the fixation to the lead connected to the lead extension.

FIG. 14B shows a connector block 1600' that includes a conical surface 1613' where the slope of the conical surface 1613' extends down to the point where the ring 1626 is present. Thus, as the grip portion 1604 is moved toward the connector block 1600' such as by turning the grip portion 1604, the slope of the conical portion of the deformable portion 1605' engages the slope of the conical surface 1613' thereby causing the conical portion of the deformable portion 1605' to be forced toward and eventually contact the ring 1626. This contact against the ring 1626, which is typically a rigid material such as a biocompatible metal, provides fixation of the lead 1628 within the connector block 1600' without the conical portion of the deformable portion 1605' contacting the lead body that is typically a polymer that is softer than the ring 1626.

In these prior examples of connector blocks having fixation structures, the grip portion of the fixation structure has been described as providing a function like a nut by being threaded onto matching threads on the nose structure. However, other forms of the grip portion are also possible for these various examples that may or may not include threads. Likewise, the nose structure of these examples may or may not utilize threads. For instance, the grip portion could have other structures that lock to structures of the nose structure of the connector block upon a clinician manipulating the grip portion by forcing the grip portion to move toward the nose structure, which in turn causes the deformation of the deformable portion of the fixation structure that creates contact with the lead to provide fixation of the lead within the connector block.

Other modifications are also possible. For example, the connector blocks 1500 and 1600 discussed above are shown as having a single lead bore and therefore a single lead fixation configuration of the fixation structure including the grip portion and the retained ferrule portion or retained deformable portion. However, it will be appreciated that connector blocks 1500 and 1600 may be provided with multiple lead bores where a grip and deformable structure is provided for each bore so that each lead may be individually fixed in place and removed by manipulation of the corresponding grip.

To ensure that grip portion in the several preceding examples maintains a tightened position to maintain fixation to the medical lead, mating structures such as holes and a detent may be provided on the grip portion and on the connector block, respectively. Once the grip portion is tightened, a detent engages a particular hole which prevents the grip portion from turning during normal use but may be turned when force is being applied by a user. While a single detent may be used, it will be appreciated that multiple detents may be present and may be spaced in correspondence with the spacing of the corresponding holes. Additionally, the position of the detent(s) and the holes may instead be swapped where the detent(s) are present on the radial surface of the grip portion while the holes are present on the nose structure.

Figure 15:
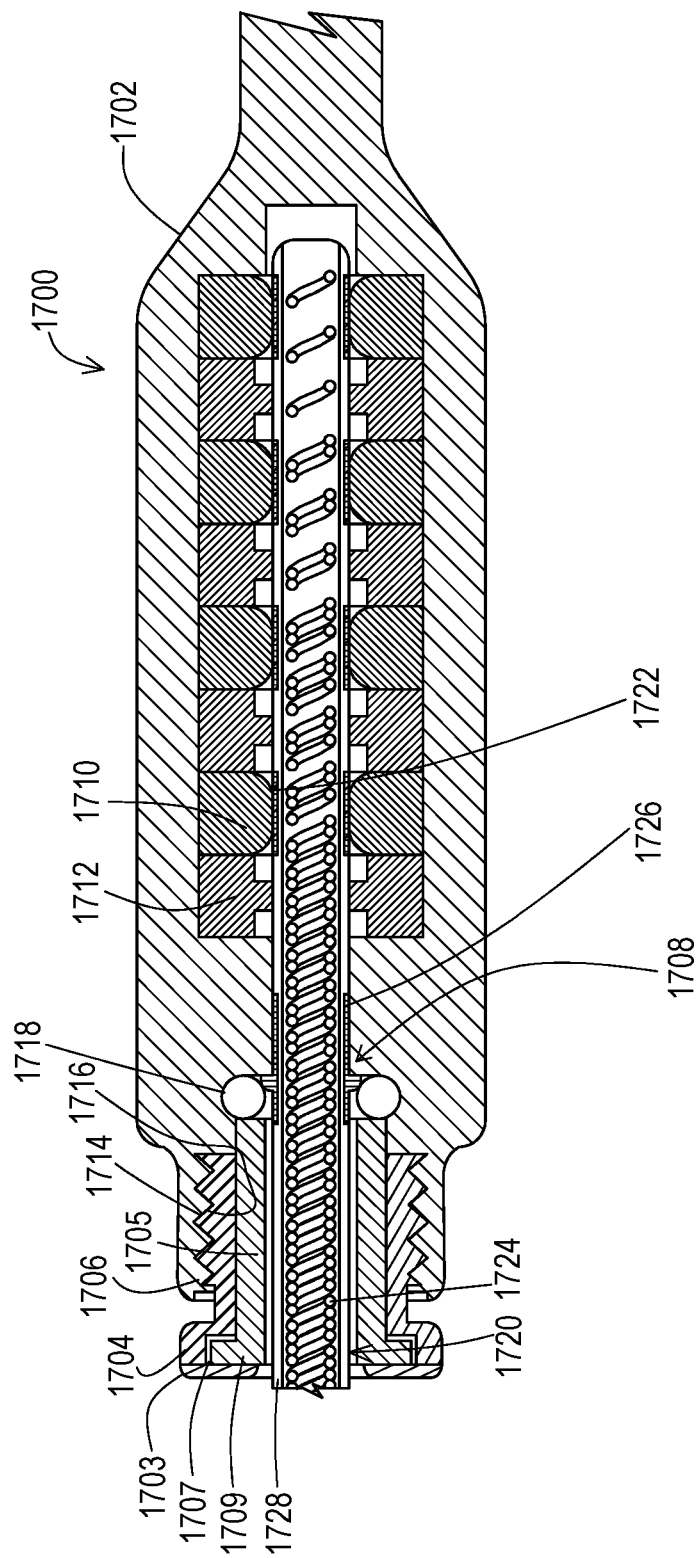
FIG. 15 shows a cross-sectional view of another example of a fixation structure with a retained ferrule portion and an associated connector block of a lead extension that has a deformable structure that provides fixation to a medical lead within the connector block upon the fixation structure causing compression of the deformable structure.

FIG. 15 shows a cross-sectional view of a second example of a connector block 1700 with a design that utilizes a fixation structure and a separate deformable structure for lead fixation. The fixation structure includes a grip portion 1704, a cap 1703 attached to the grip portion to define a recess 1707, and a ferrule portion 1705 with a flange 1709 retained within the recess 1707. The connector block 1700 includes a housing 1702, and within the housing 1702 a bore 1708 is defined by a nose structure 1706 affixed or integral to the housing 1702 and a series of interleaved seals 1712 and electrical connectors 1710. A proximal end of the lead 106 having lead body 1728 has been inserted into a bore 1720 of a grip portion 1704 of the fixation structure and further into the bore 1708 of the remainder of the connector block 1700. The electrical connectors 1710 make physical contact with electrical contacts 1722 of the lead 106, and conductors 1724 of the lead 106 are electrically coupled with corresponding electrical contacts 1722 such that the conductors 1724 are electrically coupled with the connectors 1710. The conductors 1724 extend to the distal end of the lead 106 (not shown in FIG. 15) where they are electrically coupled to corresponding electrodes 108.

In this example, the lead 106 includes a ring 1726 that has a flange that provides a hard stop for the lead 106 within the bore 1708. The nose structure 1706 is provided with an engagement surface 1714, which in this example is an interior threaded surface, and the grip portion 1704 is likewise provided with an exterior threaded surface 1716 that threads onto the surface 1714. Therefore, the grip portion 1704 in this example tightens against the nose structure 1706 when turned a given direction.

A deformable structure 1718, which in this example is also an elastomeric O-ring, is positioned between a blunt end of the ferrule portion 1705 and an internal surface of the nose structure 1706. As the grip portion 1704 is manipulated by being turned in the tightening direction, the retained ferrule portion 1705 moves toward the nose structure 1706 and therefore compresses the deformable structure 1718. The deformable structure 1718 then deforms to shrink in the direction of movement of the ferrule portion 1705 but to grow in a direction perpendicular to the direction of movement of the ferrule portion 1705 which is a radial direction of the bore 1708.

By growing in the radial direction of the bore 1708, the deformable structure 1718 creates a force in that radial direction by pressing against the lead 106. In this example, the deformable structure 1718 presses against the metal ring 1726 of the lead 106, but it will be appreciated that the deformable structure 1718 may be positioned to contact the lead body directly instead. This force against the lead 106 creates a high degree of friction between the deformable structure 1718 and the ring 1726 which provides fixation of the lead 106 within the connector block 1700. Additionally, the pressure of the deformable structure against the lead 106 presents a seal to restrict fluid ingress.

Figure 16:
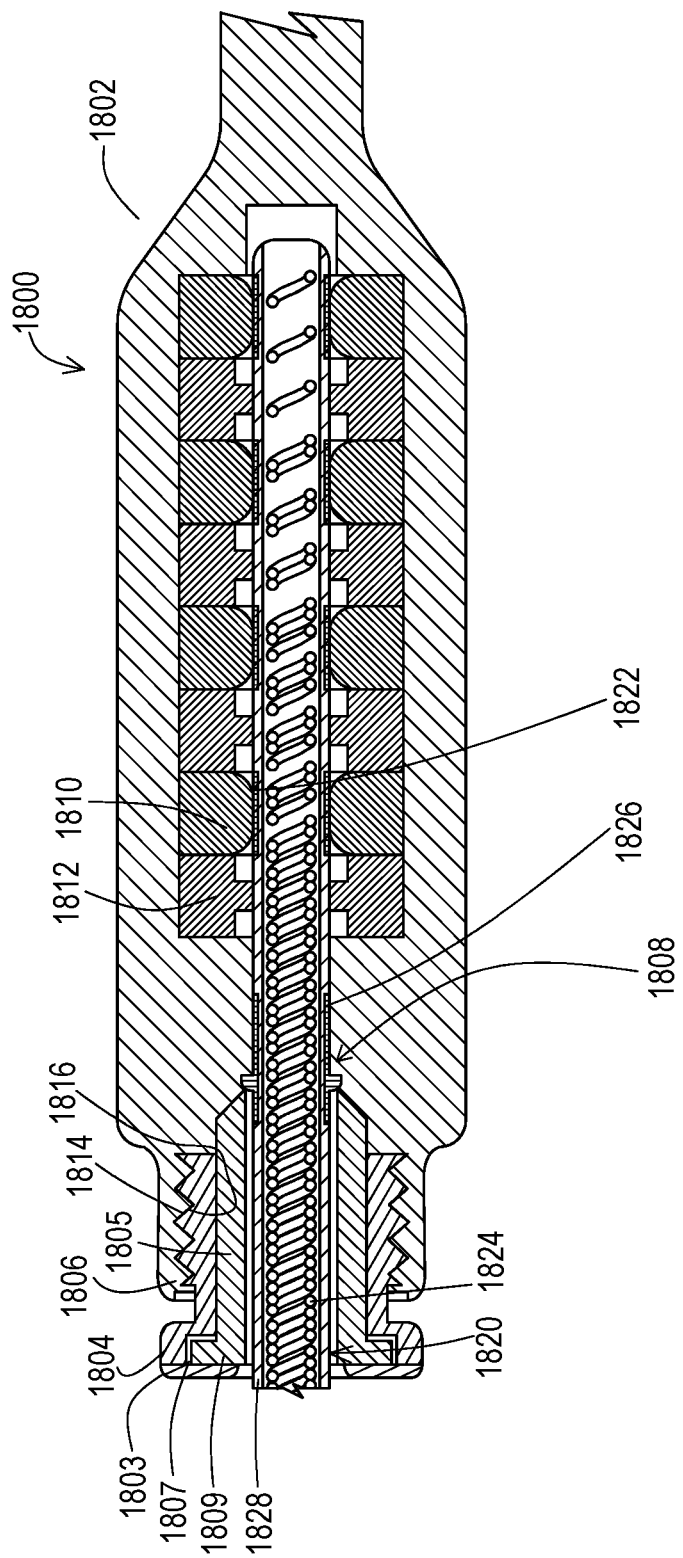
FIG. 16 shows a cross-sectional view of another example of a fixation structure and an associated connector block of a lead extension where the fixation structure includes a retained deformable portion that provides fixation to a medical lead within the connector block.

FIG. 16 shows a cross-sectional view of another example of a connector block 1800 with a design that utilizes a retained deformable portion 1805 of a fixation structure for lead fixation. The fixation structure includes a grip portion 1804, a cap 1803 attached to the grip portion to define a recess 1807, and a deformable portion 1805 with a flange 1809 retained within the recess 1807. The connector block 1800 includes a housing 1802, and within the housing 1802 a bore 1808 is defined by a nose structure 1806 affixed or integral to the housing 1802 and a series of interleaved seals 1812 and electrical connectors 1810. A proximal end of the lead 106 having lead body 1828 has been inserted into a bore 1820 of the grip portion 1804 of the fixation structure. The electrical connectors 1810 make physical contact with electrical contacts 1822 of the lead 106, and conductors 1824 of the lead 106 are electrically coupled with corresponding electrical contacts 1822 such that the conductors 1824 are electrically coupled with the connectors 1810. The conductors 1824 extend to the distal end of the lead 106 (not shown in FIG. 16) where they are electrically coupled to corresponding electrodes 108.

In this example, the lead 106 includes a ring 1826 that has a flange that provides a hard stop for the lead 106 within the bore 1808. The nose structure 1806 is provided with an engagement surface 1814, which in this example is an interior threaded surface, and the grip portion 1804 is likewise provided with an exterior threaded surface 1816 that threads onto the surface 1814. Therefore, the grip portion 1804 in this example tightens against the nose structure 1806 when turned a given direction.

The deformable portion 1805 moved further into the bore as the grip portion 1804 is tightened so that the deformable portion 1805 engages an internal surface of the nose structure 1806. As the grip portion 1804 is manipulated by being further turned in the tightening direction, the deformable portion 1805 then compresses in the radial direction of the bore 1808 to create a force in that radial direction by pressing against the lead 106. In this example, the deformable portion 1805 presses against the metal ring 1826 of the lead 106, but it will be appreciated that the deformable portion 1805 may be positioned to contact the lead body directly instead. This force against the lead 106 creates a high degree of friction between the deformable portion 1805 and the ring 1826 which provides fixation of the lead 106 within the connector block 1800.

Figure 17A:
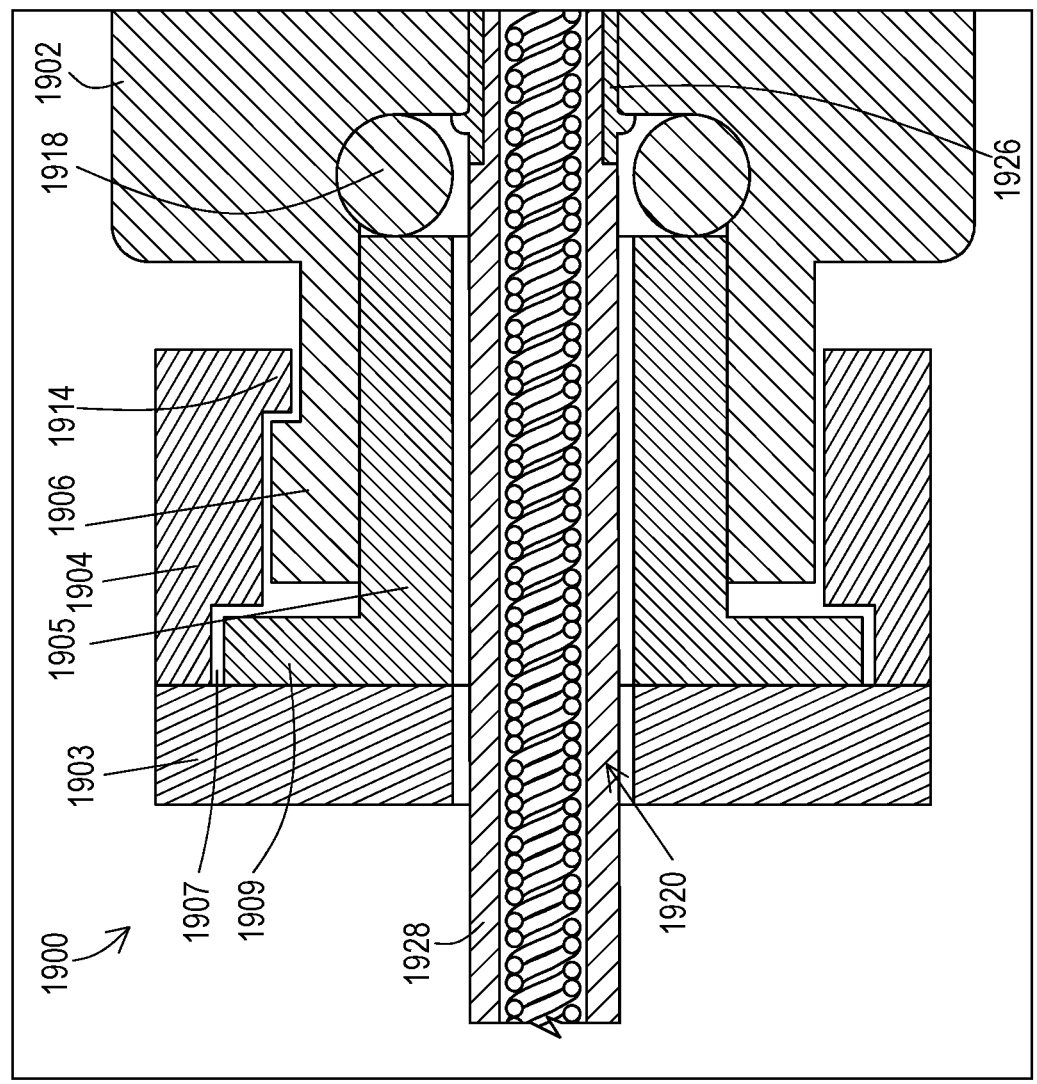
FIG. 17A shows a cross-sectional view of an example of a fixation structure that includes a retained ferrule and that utilizes a twist lock to secure the position of the grip portion and thereby maintain fixation of a medical lead within the connector block.
Figure 17B:
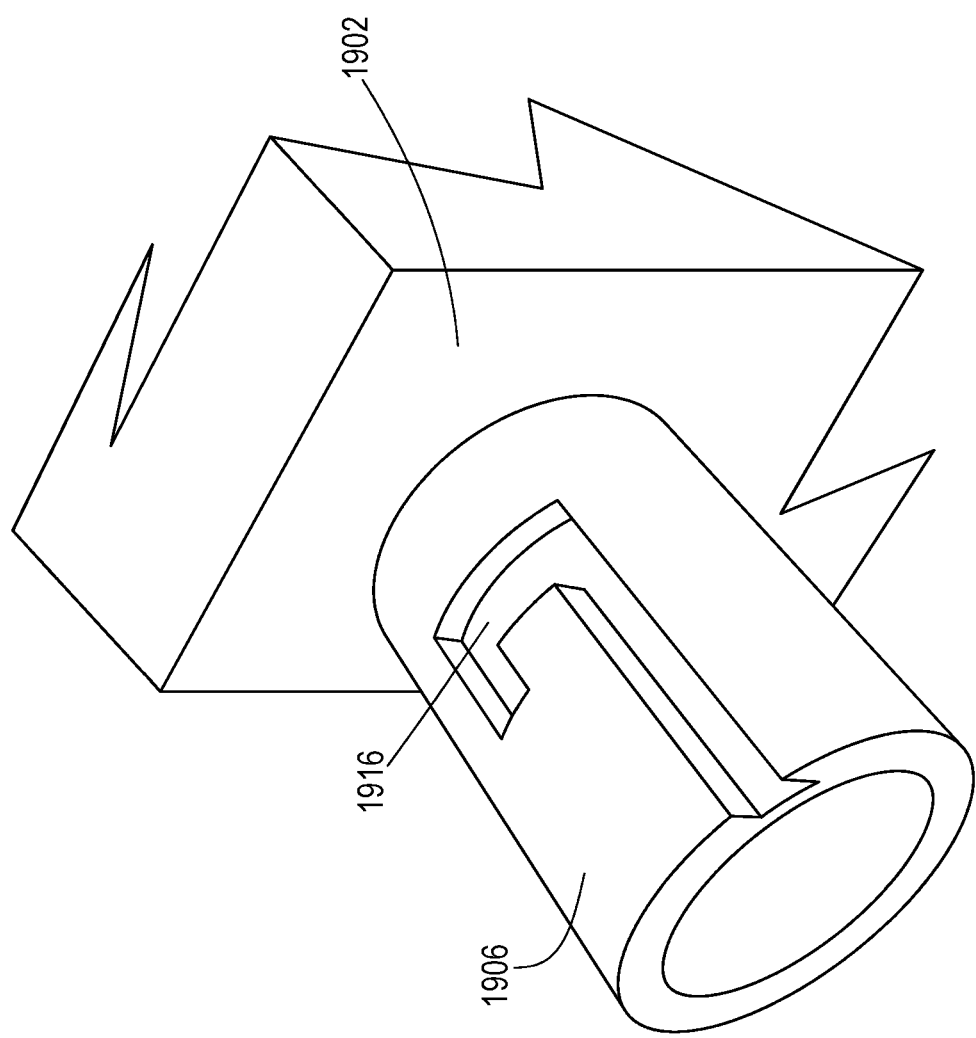
FIG. 17B shows a perspective view of the lead extension of the example of FIG. 17A to further illustrate a slot that provides the twist lock in conjunction with the grip portion.

FIGS. 17A and 17B show an example where a twist locking grip portion is used for the fixation structure of the connector block instead of a threaded grip portion. The housing 1902 of the connector block 1900 of a medical device includes the deformable structure 1918 that engages the lead 1928, such as at the connector 1926 to provide fixation. The fixation structure includes a grip portion 1904 and retained ferrule portion 1905. A flange 1909 of the ferrule portion 1905 rests within a recess 1907 of the grip portion 1904 and a cap 1903 retains the flange 1909.

The translation of the grip portion 1904 due to force by a user causes translation of the ferrule portion 1905 which is forced into the deformable structure 1918 to cause compression onto the lead 1928 that passes through the bore 1920. Rather than threading the grip portion 1904 onto the nose structure 1906, the grip portion 1904 includes a protrusion 1914 that engages and travels along a slot 1916 present on the nose structure 1906. As can be seen in FIG. 17B, the slot 1916 has a turn that establishes a locked position when the protrusion 1914 is forced as far as possible toward the housing 1902, is then twisted as far as possible within the slot 1916, and is thereafter released. There is a slight amount of over pressure applied to the deformable structure 1918 during the twisting motion and then the pressure is reduced slightly to the normal lead fixation pressure once the grip portion 1904 is released into the locked position provided by the turn in the path of slot the 1916.

While the twist of the grip portion 1904 to the locked position in the path of the slot 1916 is a counter-clockwise twist as shown in FIG. 17B, it will be appreciated that the path of the slot 1916 could instead provide for a clockwise twist to lock the position of the grip portion 1904. Additionally, the provide additional back pressure on the grip portion 1904 to further hold the grip portion 1904 in the locked position provided by the path of the slot 1916, a washer may be positioned between the connector block 1900 and the grip portion 1904. This washer may be a lock washer, a Bellevue washer, and the like to provide the back pressure onto the grip portion 1904. Additionally, the washer may be attached to the grip portion 1904, attached to the connector block 1900, or may exist as a separate object positioned between the grip portion 1904 and connector block 1900. Furthermore, it will be appreciated that such a washer may be included in the prior embodiments also in order to create pressure and friction against the threaded grip portions in order to resist the loosening of the grip portions.

Figure 18:
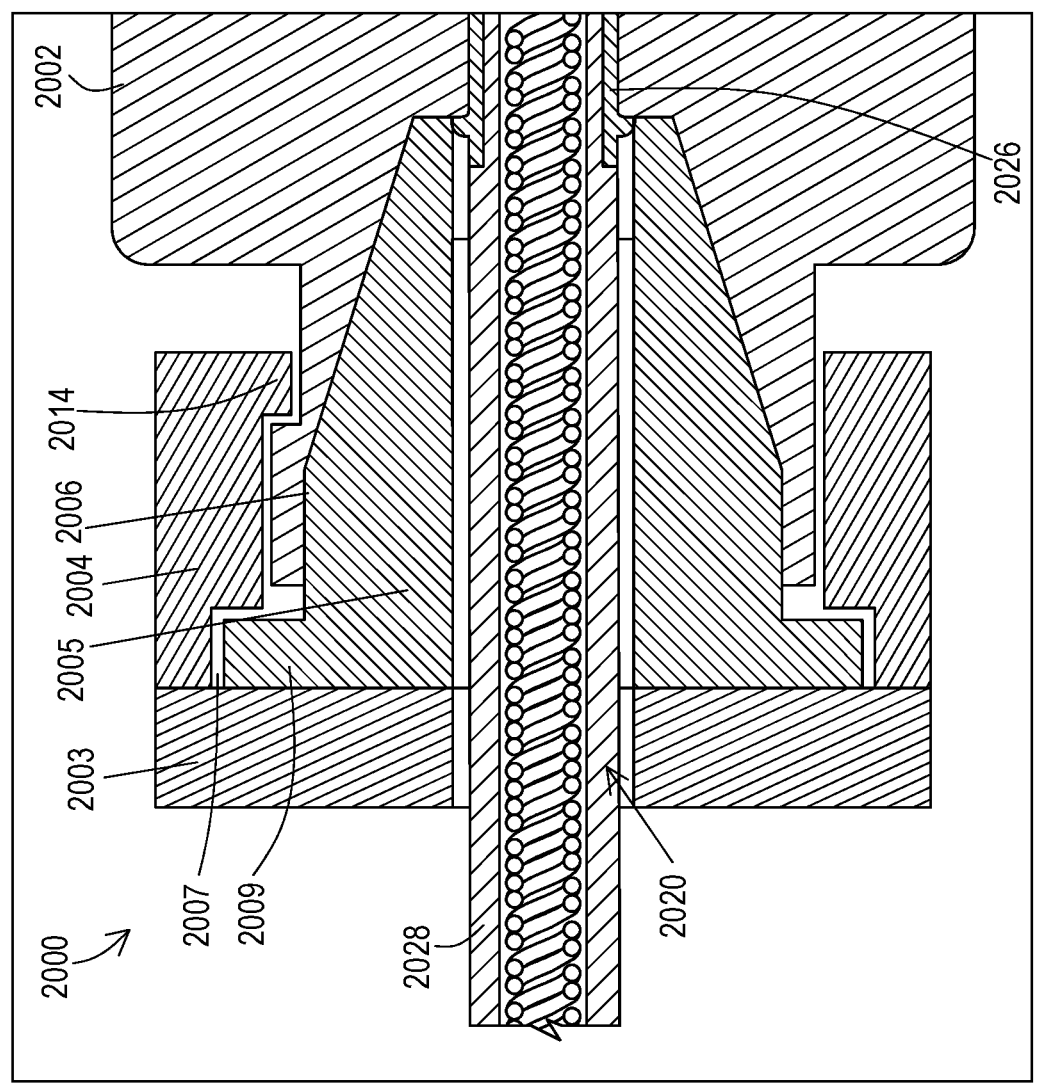
FIG. 18 shows a cross-sectional view of an example of a fixation structure that includes a retained deformable portion and that utilizes a twist lock to secure the position of the grip portion relative to a lead extension with a twist lock slot as shown in FIGS. 17A and 17B and thereby maintains fixation of a medical lead.

FIG. 18 shows another example where a twist locking grip portion is used for the fixation structure instead of a threaded grip portion. The housing 2002 of the connector block 2000 of a medical device receives a retained deformable portion 2005 of a fixation structure that also includes a grip portion 2004. A flange 2009 of the deformable portion 2005 rests in a recess 2007 of the grip portion 2004 and is retained by the presence of a cap 2003 joined to the grip portion 2004.

The translation of the grip portion 2004 due to force by a user causes translation of the deformable portion 2005 which is forced into the conical portion of the bore of the connector block 2000 to cause compression of a conical portion of the deformable portion 2005 onto the lead 2028 that passes through the bore 2020. In this example, the deformable portion 2005 engages the lead 2028 at a connector 2026 to provide fixation. Rather than threading the grip portion 2004 onto the nose structure 2006, the grip portion 2004 includes a protrusion 2014 that engages and travels along a slot, such as the slot 1916 of FIG. 17B, that is present on the nose structure 2006 so that the grip portion 2004 is locked into position in the same manner described above for the grip portion 1904 of FIG. 17A.

While embodiments have been particularly shown and described, it will be understood by those skilled in the art that various other changes in the form and details may be made therein without departing from the spirit and scope of the invention.

What is claimed is:

1. A method of fixing a proximal end of medical lead into a bore of a medical device, comprising:
   inserting the proximal end of the medical lead into the bore; and
   applying force to a fixation structure that is movable relative to the bore, the fixation structure including a grip portion that receives the applied force and a deformable portion that is retained by the grip portion and that is within and constrained relative to the bore by the medical device, wherein applying force to the fixation structure causes compression of the deformable portion so that the deformable portion engages the lead within the bore to fix the position of the lead as the deformable portion compresses.

2. The method of claim 1, wherein the grip portion includes threads that engage threads of the medical device, and wherein applying force to the fixation structure comprises turning the grip portion so that the threads of the grip portion that are engaged with the threads of the medical device cause the grip portion to translate such that the deformable portion moves further into the bore.

3. The method of claim 2, wherein the grip portion is rotatable relative to the deformable portion so that turning of the grip portion does not cause turning of the deformable portion.

4. The method of claim 1, wherein the deformable portion comprises a conical portion that engages a conical portion of the medical device and that applies a force in a radial direction of the bore upon being compressed.

5. A medical device, comprising:
   a header block having a bore with an engagement surface and a plurality of electrical connectors within the bore;
   a fixation structure mechanically engaged with the engagement surface of the header block, the fixation structure including a grip portion and a deformable portion that is retained by the grip portion, the deformable portion providing a compression force in a radial direction of the bore when a force is applied from the grip portion to the deformable portion.

6. The medical device of claim 5, wherein the engagement surface is a threaded surface and wherein the grip portion provides a threaded surface that engages the threaded surface of the header block.

7. The medical device of claim 6, wherein the engagement surface is on an exterior of a portion of the header block and the threaded surface of the grip is on an interior portion of the grip.

8. The medical device of claim 6, wherein the engagement surface is on an interior of a portion of the header block and the threaded surface of the grip is on an exterior portion of the grip.

9. The medical device of claim 5, wherein the deformable portion comprises a conical portion that engages a conical portion of the header block and that applies a force in a radial direction of the bore upon being compressed.

10. The medical device of claim 9, wherein the conical portion of the deformable portion comprises slits.

11. The medical device of claim 5, wherein a housing of the header block is a polymer.

12. The medical device of claim 5, wherein a housing of the header block is a metal.

13. The medical device of claim 5, wherein the deformable portion contacts the lead body directly.

14. The medical device of claim 5, further comprising a metal ring on the lead and wherein the deformable portion contacts the metal ring.

15. The medical device of claim 5, wherein the grip portion includes a body and a cap welded to the body, the body and the cap creating a recess where a flange of the deformable portion is located and retained.

16. A medical system, comprising:
   a medical device having a stimulation circuit and a header block, the header block having a bore with an engagement surface and a plurality of electrical connectors within the bore that are electrically coupled to the stimulation circuit;
   the medical device further comprising:
      a fixation structure mechanically engaged with the engagement surface of the header block, the fixation structure including a grip portion and a deformable portion that is retained by the grip portion and is constrained by the header block, the deformable portion providing a compression force in a radial direction of the bore when a force is applied from the grip portion to the deformable portion; and
   a medical lead having a lead body surrounding electrical conductors, the lead body having a proximal region positioned within the bore of the header block, the proximal region having a plurality of contacts that engage corresponding electrical connectors in the bore and engage the conductors within the lead body, the deformable portion of the fixation structure being compressed into contact with a portion of the proximal region of the medical lead to fix the medical lead within the bore.

17. The medical system of claim 16, wherein the engagement surface is a threaded surface and wherein the grip portion provides a threaded surface that engages the threaded surface of the header block.

18. The medical system of claim 17, wherein the engagement surface is on an exterior of a portion of the header block and the threaded surface of the grip is on an interior portion of the grip portion.

19. The medical system of claim 17, wherein the engagement surface is on an interior of a portion of the header block and the threaded surface of the grip is on an exterior portion of the grip portion.

20. The medical system of claim 16, wherein the deformable portion comprises a conical portion that engages a conical portion of the header block and that applies a force in a radial direction of the bore upon being compressed.

* * * * *